(12) United States Patent
Cheng et al.

(10) Patent No.: US 6,587,703 B2
(45) Date of Patent: Jul. 1, 2003

(54) SYSTEM AND METHOD FOR MEASURING ABSOLUTE OXYGEN SATURATION

(75) Inventors: Xuefeng Cheng, Milpitas, CA (US); Xiaorong Xu, Menlo Park, CA (US); Shuoming Zhou, Cupertino, CA (US); Lai Wang, Cupertino, CA (US)

(73) Assignee: Photonify Technologies, Inc., Sunnyvale, CA (US)

( * ) Notice: Subject to any disclaimer, the term of this patent is extended or adjusted under 35 U.S.C. 154(b) by 0 days.

(21) Appl. No.: 09/877,515

(22) Filed: Jun. 7, 2001

(65) Prior Publication Data

US 2002/0058865 A1 May 16, 2002

Related U.S. Application Data

(63) Continuation-in-part of application No. 09/664,972, filed on Sep. 18, 2000.

(51) Int. Cl.[7] .................................. A61B 5/50
(52) U.S. Cl. ................ 600/310; 600/322; 600/328
(58) Field of Search ................ 600/310, 322, 600/328, 336, 473, 475, 476; 356/39, 41; 250/339.01, 339.02, 339.05, 339.06, 339.11, 340, 341.1, 341.2

(56) References Cited

U.S. PATENT DOCUMENTS

| | | |
|---|---|---|
| 3,963,351 A | 6/1976 | Chance et al. |
| 4,555,179 A | 11/1985 | Langerholc et al. |
| 4,810,875 A | 3/1989 | Wyatt |
| 4,829,184 A | 5/1989 | Nelson et al. |
| 5,119,815 A | 6/1992 | Chance |
| 5,137,355 A | 8/1992 | Barbour et al. |
| 5,167,230 A | 12/1992 | Chance |
| 5,402,778 A | 4/1995 | Chance |
| 5,555,885 A | 9/1996 | Chance |

(List continued on next page.)

OTHER PUBLICATIONS

Chance et al., "New Optical Probe Designs For Absolute-(Self–Calibrating) NIR Tissue Hemoglobin Measurements" SPIE Conference on Optical Tomography and Spectroscopy of Tissue III, SPIE vol. 3597, Jan. 1999, pp. 618–631.

(List continued on next page.)

*Primary Examiner*—Eric F. Winakur
(74) *Attorney, Agent, or Firm*—Ritter, Lang & Kaplan LLP

(57) ABSTRACT

The present invention generally relates to apparatus and methods for obtaining absolute values of concentrations of chromophores of a medium and/or absolute values of their ratios. In particular, the present invention relates to continuous wave spectroscopic optical systems and methods for determining the absolute values of deoxygenated and/or oxygenated hemoglobins and their ratios in a physiological medium. The optical system typically includes (1) a source module optically coupling with the medium and irradiating into the medium multiple sets of electromagnetic waves with different wave characteristics, (2) a detector module optically coupling with the medium and detecting electromagnetic waves, and (3) a processing module operatively coupling with the detector module, and determining the absolute values of the concentrations and the ratios thereof from multiple wave equations applied to the source and detector modules. The processing module is designed to obtain such absolute values by a method typically including the steps of (1) obtaining multiple sets of wave equations, (2) eliminating source-dependent and detector-dependent parameters therefrom to obtain a set of intermediate equations, (3) providing a correlation between medium-dependent and geometry-dependent parameters and the chromophore concentrations or ratios thereof, (4) incorporating the correlation into the set of intermediate equations, and (5) obtaining the absolute values of the chromophore concentrations and ratios thereof.

49 Claims, 9 Drawing Sheets

U.S. PATENT DOCUMENTS

| | | |
|---|---|---|
| 5,564,417 A | 10/1996 | Chance |
| 5,596,987 A | 1/1997 | Chance |
| 5,664,574 A | 9/1997 | Chance |
| 5,676,143 A | 10/1997 | Simonsen et al. |
| 5,782,755 A | 7/1998 | Chance et al. |
| 5,792,051 A | 8/1998 | Chance |
| 5,803,909 A | 9/1998 | Maki et al. ............ 600/310 |
| 5,807,263 A | 9/1998 | Chance |
| 5,820,558 A | 10/1998 | Chance |
| 5,835,617 A | 11/1998 | Ohta et al. |
| 5,853,370 A | 12/1998 | Chance et al. |
| 5,865,754 A | 2/1999 | Sevick-Muraca et al. |
| 5,873,821 A | 2/1999 | Chance et al. |
| 5,899,865 A | 5/1999 | Chance |
| 5,917,190 A | 6/1999 | Yodh et al. |
| 5,954,053 A | 9/1999 | Chance et al. |
| 5,987,346 A | 11/1999 | Benaron et al. ......... 600/407 |
| 5,987,351 A | 11/1999 | Chance |
| 6,058,324 A | 5/2000 | Chance |
| 6,078,833 A * | 6/2000 | Hueber ................. 600/476 |
| 6,088,605 A | 7/2000 | Griffith et al. ......... 600/316 |
| 6,104,945 A | 8/2000 | Modell et al. .......... 600/473 |
| 6,134,460 A | 10/2000 | Chance |
| 6,151,518 A * | 11/2000 | Hayashi ................ 600/322 |
| 6,192,260 B1 | 2/2001 | Chance |
| 6,272,367 B1 | 8/2001 | Chance |
| 6,304,771 B1 | 10/2001 | Yodh et al. |

OTHER PUBLICATIONS

Chance et al., 1998, "A novel method for fast imaging of brain function, non–invasively with light," *Optics Express* 2(10):411–423.

Cubeddu et al., 1998, "In vivo absorption and scattering spectra of human tissues in the red and near infrared," *TOPS* 21:271–274.

Du et al., 1998, "Quantitative detection of hemoglobin saturation on piglet brain by near–infrared frequency–domain spectroscopy," *Proceedings of Photon Propagation in Tissues III (SPIE)* 3194:55–62.

Fantini et al., 1999, "Non–invasive optical mapping of the piglet brain in real time," *Optics Express* 4(8):308–314.

Ma et al., "Quantitative study of hypoxia stress in piglet brain by IQ phase modulation oximetry," *Part of the SPIE Conference on Optical Tomography and Spectroscopy of Tissue III*, San Jose, California, Jan. 1999. SPIE vol. 3597, pp. 642–649.

Pogue et al., 1997, "Instrumentation and design of a frequency–domain diffuse optical tomography imager for breast cancer detection," *Optics Express* 1(13):391–403.

Siegel et al., "Diffuse optical tomography of rat brain function," *Part of the SPIE Conference on Optical Tomography and Spectroscopy of Tissue III*, San Jose, California. Jan. 1999. SPIE vol. 3597, pp. 252–261.

* cited by examiner

SYSTEM AND METHOD FOR MEASURING ABSOLUTE OXYGEN SATURATION

CROSS-REFERENCE TO RELATED APPLICATIONS

The present application is a continuation-in-part application of U.S. non-provisional patent application entitled "A System and Method for Absolute Oxygen Saturation," Ser. No. 09/664,972, filed on Sep. 18, 2000.

FIELD OF THE INVENTION

The present invention generally relates to apparatus and methods for determining absolute values of various properties of a physiological medium. In particular, the present invention relates to non-invasive optical systems and methods for determining absolute values of concentrations of oxygenated and deoxygenated hemoglobins (and/or their ratios). The present invention also relates to apparatus and methods for obtaining such absolute values by solving generalized photon diffusion equations and their simplified variations such as modified Beer-Lambert equations.

BACKGROUND OF THE INVENTION

Near-infrared spectroscopy has been used for non-invasive measurement of various physiological properties in animal and human subjects. The basic principle underlying the near-infrared spectroscopy is that physiological tissues include various highly-scattering chromophores to the near-infrared waves with relatively low absorption. Many substances in a physiological medium may interact or interfere with the near-infrared light waves that propagate therethrough. Human tissues and cells, e.g., include numerous chromophores such as oxygenated hemoglobins, deoxygenated hemoglobins, water, cytochromes, and lipids, where the hemoglobins are the dominant chromophores in the spectrum range of 700 nm to 900 nm. Accordingly, the near-infrared spectroscopy has been applied to measure oxygen levels in the medium such as tissue hemoglobin oxygen saturation (abbreviated as "oxygen saturation" hereinafter) and total hemoglobin concentrations. Various techniques have been developed for the near-infrared spectroscopy, e.g., time-resolved spectroscopy (TRS), phase modulation spectroscopy (PMS), and continuous wave spectroscopy (CWS).

The TRS technology is based on operational principles such as pulse-time measurements and pulse-code modulation. In particular, it measures a time delay between an entry and an exit of electromagnetic waves to and from the physiological medium. Typically, the TRS applies to the medium an impulse or pulse sequence of electromagnetic waves having a duration in the order of a few pico-seconds. Photon diffusion encodes tissue characteristics not only in the timing of the delayed pulse received by a detector, but also in the received intensity time profile. Therefore, instead of receiving a "clean" replica of the transmitted pulse, the return signals are spread out in time, and have greatly reduced amplitudes. Accordingly, the TRS measures the intensity of the return signals over a finite period of time, which is long enough to detect an entire portion of the delayed return signals. Based on such shape changes and amplitude attenuation of the input impulse or pulse, different times of arrival of photons and the mean time delay between the light (or wave) source and detector are used to obtain the tissue absorption and tissue scattering through, e.g., deconvolution of the return signals. Information on the tissues traversed (such as optical pathlengths and their changes) is then readily obtained. Details of the TRS technology are provided, for example, in D. A. Boas et al., Proc. Natl. Acad. Sci., vol. 91, p. 4887 (1994); R. P. Spencer and G. Weber, Ann. (N.Y.) Acad. Sci., vol. 158, p. 3631 (1996); and J. Sipior et al., Rev. Sci. Instrum., vol. 68, p. 2666 (1997), all of which are incorporated herein by reference for background.

The PMS technology employs phase-modulated electromagnetic waves irradiated by the wave source and transmitted through the physiological medium. Typical examples of PMS include homodyne systems, heterodyne systems, single side-band systems, and other systems based on transmitter-receiver cross-coupling and phase correction algorithms. Like TRS, PMS systems monitor the intensities of the attenuated electromagnetic waves. In addition, it is necessary for the PMS system to measure frequency-domain parameters, such as phase shift of the electromagnetic waves which is independent of the wave intensities. Based on such time-domain and frequency-domain information, PMS systems determine spectra of an absorption coefficient and/or scattering coefficient of the chromophores of the medium, and calculate absolute values of the hemoglobin concentrations. Details of the PMS technology are provided, for example, in U.S. Pat. No. 5,820,558 and a technical article by B. Chance et al. in Rev. Sci. Instrum., vol. 69, p. 3457 (1998), both of which are incorporated herein by reference in their entirety.

By contrast, CWS systems employ electromagnetic waves that are non-impulsive and not phase modulated. That is, CWS systems apply to the medium electromagnetic waves having at least substantially identical amplitude over a measurable period of time. On the detection side, CWS systems only measure intensities of the irradiated and detected electromagnetic waves and does not assess any frequency-domain parameters thereof.

In a homogeneous and semi-infinite medium model, both of the TRS and PMS have been used to obtain spectra of an absorption coefficient and (reduced) scattering coefficient of the physiological medium by solving a photon diffusion equation, and to calculate the absolute values of the concentrations of oxygenated and deoxygenated hemoglobins as well as tissue oxygen saturation. Despite their capability of providing such absolute values of the hemoglobin concentrations and the oxygen saturation, one major drawback of TRS and PMS is that the TRS equipment requires a pulse generator and detector and that the PMS needs additional hardware and signal processing capabilities to determine frequency-domain parameters. Accordingly, in practice both TRS and PMS systems are bulky and expensive. To the contrary, the CWS may be manufactured at a lower cost because all it needs to do is to perform intensity measurement. However, prior art CWS technology was limited in its utility because it can only provide the relative values or changes in the oxygenated and deoxygenated hemoglobin concentrations. Therefore, the conventional CWS cannot estimate the tissue oxygen saturation from such changes in the hemoglobin concentrations. Thus, there is a need for novel CWS systems and methods for measuring absolute value of concentrations of the hemoglobins and the oxygen saturation in the physiological medium.

SUMMARY OF THE INVENTION

The present invention generally relates to apparatus and methods for obtaining the absolute values of concentrations of chromophores of a medium and/or absolute values of their ratios. More particularly, the present invention relates to non-invasive optical systems and methods based on continuous wave spectroscopy (CWS) methods for determining absolute values of concentrations of the oxygenated and deoxygenated hemoglobins and their ratios in a physiological medium.

In general, wave propagation or photon migration in a medium is described by a generalized photon diffusion equation:

$$I = \alpha \cdot \beta \cdot \gamma \cdot I_o \cdot e^{\{-B \cdot L \cdot \delta \cdot \Sigma_i(\varepsilon_i C_i) + \sigma\}} \quad (1)$$

where "$I_0$" is a system variable representing an intensity of the electromagnetic waves or photons (e.g., in the near-infrared ranges) irradiated by a wave source and where "I" is another variable denoting an intensity of the electromagnetic waves detected by a wave detector. Parameter "$\alpha$" is generally associated with the wave source and medium and accounts for, e.g., characteristics of the wave source such as irradiation power and configuration thereof, mode of optical coupling between the wave source and medium, and/or optical coupling loss therebetween. Parameter "$\beta$" is generally associated with the wave detector and medium and accounts for, e.g., characteristics of the wave detector such as detection range and sensitivity, optical coupling mode between the wave detector and medium, and associated coupling loss. Parameters "$\alpha$" and "$\beta$" may also depend upon, to some extent, other system characteristics and/or optical properties of the medium, including those of chromophores included therein. Parameter "$\gamma$" may be either a proportionality constant (including, e.g., 1.0) or a system parameter which may change its value according to the characteristics of the wave source, wave detector, chromophores, and/or medium. Parameter "B" generally accounts for lengths of optical paths of photons or electromagnetic waves traversed through the medium, and is predominantly determined by the optical properties of the medium. However, an exact value of parameter "B" may also depend on the characteristics of the wave source and/or detector as well. A typical example of such parameter "B" is conventionally known as a path length factor. It is noted that the parameter "B" may also take the value of 1.0 where the generalized diffusion equation (1) is approximated to the Beer-Lambert equation. To the contrary, parameter "L" is generally geometry-dependent and accounts for a (linear) distance between a particular wave source and a matching wave detector operatively coupled to each other. Parameter "$\delta$" may be either a proportionality constant (including, e.g., 1.0) or a system parameter that may depend on the characteristics wave source, wave detector, and/or medium. Parameter "$\varepsilon_i$" accounts for an optical interaction and/or interference of photons or electromagnetic waves with an i-th chromophore included in the medium. It is noted that, depending upon the definition and value of the parameter "$\delta$", the parameter "$\varepsilon_i$" may represent an extinction coefficient, an absorption coefficient, a scattering coefficient, and/or a reduced scattering coefficient of the medium or the chromophores included therein. Variable "$C_i$" represents concentration of the i-th chromophore included in the medium, and parameter "$\sigma$" is either a proportionality constant (including, e.g., 0.0) or a parameter which may be associated with the wave source, wave detector, and/or medium.

It will be appreciated that while the system variables such as "I" and "$I_0$" are functions of time only, other system parameters have constant values which are determined by the characteristics of the wave source, wave detector, physiological medium, and chromophores included therein. Therefore, the generalized diffusion equation (1) is a function of time and is independent of or at least substantially insensitive to frequency-domain parameters, such as the frequency and phase angle of the electromagnetic waves. Despite the numerous parameters of the generalized photon diffusion equation (1) and various modified versions thereof as will be described in greater detail below, the optical systems and methods disclosed in this invention enable the direct determination of absolute values of the chromophore concentrations and/or ratios thereof.

In one aspect of the present invention, a method is provided to solve a set of wave equations applied to an optical system having at least one wave source and at least one wave detector. Photons or electromagnetic waves are irradiated by the wave source, transmitted through the physiological medium including at least one chromophore, and detected by the wave detector. The wave equation, e.g., the generalized diffusion equation (1), expresses the intensity of electromagnetic waves detected by the wave detector (i.e., "I") as a function of system variables (e.g., "$I_0$" and "$C_i$") and system parameters (e.g., "$\alpha$," "$\beta$," "$\gamma$," "B," "L," "$\delta$," "$\varepsilon_i$," and "$\sigma$"). The method generally includes the steps of obtaining one or more sets of equations by applying the wave equation to the optical system capable of irradiating multiple sets of electromagnetic waves having different wave characteristics, eliminating the source-dependent parameter (e.g., "$\alpha$") and detector-dependent parameter (e.g., "$\beta$") therefrom to obtain a set of intermediate equations, providing at least one correlation of chromophore concentrations (and/or their ratios) with medium-dependent and geometry-dependent parameters (e.g., "B" and "L," respectively), incorporating the correlation into the set of intermediate equations, and obtaining an expression for absolute values of the concentrations of the chromophores (and/or ratios thereof) in terms of the correlation, intensities of electromagnetic waves (e.g., "I" and "$I_0$"), and medium- or chromophore-dependent parameters (e.g., "$\varepsilon_i$"). The method also includes the steps of determining a value of the correlation from a known geometric arrangement between the wave source(s) and detector(s), experimentally measuring the intensities of the electromagnetic waves (i.e., "I" and "$I_0$") determining values of medium- or chromophore dependent parameters (i.e., "$\varepsilon_i$'s"), and determining the absolute values of the concentrations of the chromophores (and/or ratios thereof) therefrom.

This embodiment of the present invention offers several benefits over the prior art CWS technology, which is capable of measuring only the changes (i.e., differential or relative values) in the chromophore concentrations. In particular, the foregoing as well as the following embodiments of the present invention allow determination of such values and/or ratios only by measuring the intensities of the electromagnetic waves irradiated by the wave source and detected by the wave detector. Accordingly, the present invention does not require bulky, complex, and/or expensive electronic parts to measure temporally perturbed pulse signals of a short duration (as used in TRS) and to assess frequency-domain parameters of the electromagnetic waves (as used in PMS). For example, the embodiments of the present invention provide direct means for assessing the "absolute values" of the chromophore concentrations as well as their ratios in various physiological media, e.g., tissues or cells in organs, muscles, and/or body fluids. In addition, as will be described in detail below, the foregoing method of the present invention can be readily applied into optical probes having any arbitrary number of wave sources and/or detectors arranged in any arbitrary configuration. Furthermore, the foregoing embodiment of the present invention cal also be applied to any optical probes of conventional optical imaging systems including any number of wave sources and detectors arranged in any arbitrary configurations. Thus, the foregoing method allows construction of optical systems customized to specific clinical applications without compromising their performance characteristics.

Embodiments of this aspect of the present invention may include one or more of the following features.

The generalized diffusion equation (1) may be applied to an optical system with at least one wave source and at least one wave detector:

$$I_{mn} = \alpha_m \cdot \beta_n \cdot \gamma \cdot I_{o,m} \cdot e^{[-B_{mn} \cdot L_{mn} \cdot \delta \cdot \Sigma_i (\varepsilon_i C_i) + \sigma]} \quad (2)$$

where the subscripts "m" and "n" represent an m-th wave source and an n-th wave detector, respectively.

The method may include the steps of applying equation (2) to the optical system to obtain a first and a second set of equations, eliminating at least one of $\alpha_m$, $\beta_n$, $\gamma$, $\delta$, and $\sigma$ from the first and second set of equations by performing mathematical operations thereon to obtain a third set of equations, providing at least one theoretically-derived, semi-empirical or empirical correlation between the concentrations of the chromophores (or ratios thereof) and one or more terms of the third set of equations including $B_{mn}$ and/or $L_{mn}$, incorporating the above correlation into the third set of equations to replace such terms thereby, and obtaining an expression for the absolute values of the concentrations of the chromophores (and/or ratios thereof) based on the measured values of $I_{mn}$ and $I_{o,m}$ and known values of $\varepsilon_i$'s.

The foregoing method may also include the steps of applying the optical system to the physiological medium such as cells of organs, tissues, and body fluids, and determining the absolute values of the chromophore concentrations (and/or their ratios) directly from the experimentally measured values of $I_{mn}$ and $I_{o,m}$ and known values of $\varepsilon_i$'s. The measuring step may include an additional step of monitoring concentrations of oxy-hemoglobin and/or deoxy-hemoglobin, and/or a ratio thereof such as, e.g., (tissue) oxygen saturation.

The foregoing method may also include the step of determining presence of tumor cells in a finite area of the medium or determining a presence of an ischemic condition as well. In the alternative, the foregoing method may also include the steps of applying the foregoing optical system to the physiological medium including transplanted cells of organs and/or tissues and measuring absolute values of the chromophore concentrations (or their ratios) based on the measured values of $I_{mn}$ and $I_{o,m}$ and known values of $\varepsilon_i$'s. For example, the method may be used to determine presence of an ischemic condition in the transplanted organs and tissues during or after surgical procedures.

The applying step of the foregoing method may include the step of irradiating the first and second set of electromagnetic waves which can be preferably distinguished by the wave detector due to their different wave characteristics. For example, different sets of the electromagnetic waves may have different wavelengths (or frequencies), phase angles, harmonics, and/or a combination thereof. Therefore, in the irradiating step, the first set of electromagnetic waves are irradiated at a first wavelength, while the second set of electromagnetic waves has a second wavelength that is different from the first wavelength.

The eliminating step of the foregoing method may include the step of deriving at least one first ratio of two wave equations both of which are selected from one of the first and second sets of the equations. The wave equations may be applied to the same wave source but to different wave detectors, thereby eliminating $\alpha_n$, $\gamma$, and $\sigma$ from the first ratio. Alternatively, the wave equations may be applied to two different wave sources but to the same wave detector, thereby eliminating $\beta_n$, $\gamma$, and $\sigma$ from the first ratio. The eliminating step may also include the step of deriving at least one second ratio of two wave equations both of which are selected from the other of the first and second sets of the equations. A sum of or a difference between the first and second ratios may also be obtained so as to eliminate at least one of $\alpha_m$ and $\beta_n$. In the alternative, the eliminating step may include the step of approximating both parameters "$\gamma$" and "$\delta$" as a unity.

The providing step of the foregoing method may include the step of providing a formula of the medium-dependent and geometry-dependent parameters as a polynomial, sinusoid or other functions of the chromophore concentrations (and/or ratios thereof). Such a formula may also include a zero-th order term. Alternatively, the medium-dependent and geometry-dependent parameters may be approximated as a constant.

In another aspect of the present invention, an optical system is provided to determine absolute values of concentrations of chromophores and/or ratios thereof in a physiological medium. The optical system typically includes a source module, a detector module, and a processing module. The source module irradiates, into the medium, two or more sets of photons or electromagnetic radiation having different wave characteristics. The detector module detects the electromagnetic waves which are transmitted through the medium. The processing module operatively couples with the detector module and determines an absolute value of the concentration of the chromophores and/or ratios thereof from electromagnetic radiation irradiated from and detected by the source and detector modules, respectively, where such determination is based only on the intensity measurement of continuous wave electromagnetic radiation. It is noted that the source and detector modules are preferably designed to operate in a continuous-wave spectroscopy (CWS) mode.

This embodiment of the present invention offers several benefits over the prior art near-infrared spectroscopy technologies such as conventional CWS, TRS, and PMS. As discussed above, the prior art CWS can measure only relative values of or changes in the concentration of the chromophores. Therefore, the conventional CWS can neither provide the absolute values of the chromophore concentrations nor the ratios thereof such as (tissue) oxygen concentration. By contrast, the optical monitoring or imaging systems based on the present invention operating in the CWS mode can measure the absolute values of the chromophore concentrations (and their ratios) and provide images of two-dimensional or three-dimensional distribution of such absolute values. In addition, because the optical systems of the present invention only require intensity measurement of the electromagnetic radiation ($I_{mn}$ and $I_{o,m}$) without having to process the frequency-domain characteristics, they can be provided as cheap, portable, but reliable devices. In addition, when the foregoing systems of the present invention may be readily modified and applied to the conventional TRS and PMS technologies for improved accuracy and lower cost.

Embodiments of this aspect of the present invention may include one or more of the following features.

The wave source may be arranged to irradiate electromagnetic waves which can be preferably distinguished by the wave detector due to their different wave characteristics. For example, different sets of the foregoing electromagnetic waves may have different wavelengths (or frequencies), phase angles, harmonics or their combination. For example, the first set of the electromagnetic waves may have a first wavelength and a second set of said electromagnetic waves may have a second wavelength which is different from the first wavelength. In the alternative, the first set of electromagnetic waves may be carried by a first carrier wave and the second set of electromagnetic waves may be carried by a second carrier wave which has wave characteristics different from those of the first carrier wave, e.g., different wavelengths, phase angles, harmonics, etc. It is appreciated that different wave characteristics of the electromagnetic waves are necessary for the wave detector only to obtain multiple intensity signals (i.e., $I_{mn}$ and $I_{o,m}$ measured at different wavelengths) over the same sampling area of the medium. However, such different wave characteristics are not directly used to determine the absolute values of the chromophore concentration and/or their ratios.

The processing module preferably includes an algorithm to determine the absolute values of the chromophore concentrations (or their ratios) based on various system variables and/or parameters, e.g., the intensity of the electromagnetic waves irradiated by the source module, intensity of the electromagnetic waves detected by the detector module, and one or more system parameters accounting for interaction or interference of electromagnetic waves and/or photons with the medium.

The wave equations may include at least one term which is substantially dependent on the optical properties of the medium (i.e., medium-dependent) and/or on configuration of the source and detector modules (i.e., geometry-dependent). Examples of such term may include, but not limited to, "B" and "L" of equation (1) or "$B_{mn}$" and "$L_{mn}$" of equation (2). The algorithm of the processing module may include at least one correlation expressing a first function of the term as a second function of the chromophore concentrations (and/or ratios thereof). The second function may be any analytic function, e.g., a polynomial of the concentrations and/or ratios thereof. Alternatively, the algorithm may also be arranged to approximate the second function as a constant.

The source module may include at least one wave source, and the detector module may include at least two wave detectors. Alternatively, the source module may include at least two wave sources, while the detector module may include at least one wave detector. It is preferred, however, that both of the source and detector modules include, respectively, at least two wave sources and at least two wave detectors.

In one aspect of medical application of the present invention, the foregoing optical systems and methods therefor may be used to measure the absolute values of concentrations of oxygenated and deoxygenated hemoglobin and/or their ratio. Such optical systems will be beneficial in non-invasively diagnosing ischemic conditions and/or locating ischemia in various organs and tissues. For example, the optical system may be used to prognose or diagnose stroke, cardiac ischemia or other physiological abnormalities originating from or characterized by abnormally low concentration of oxy-hemoglobin. Accordingly, presence of cancerous tumors may be easily detected. In addition, the optical systems and methods of the present invention may be applied to tissues or cells disposed in epidermis, corium, and organs such as a lung, liver, and kidney.

In another aspect of the medical application of the present invention, the foregoing optical systems and methods therefor may be applied to measure the absolute values of the concentrations of oxy- as well as deoxy-hemoglobins to diagnose vascular occlusion during or after various surgical procedures including organ transplantation. In general, prognosis of organ transplantation depends on adequate supply of oxygenated blood to transplanted organs during and post surgical procedure. The optical systems and methods of the present invention may be applied to detect vascular occlusion in transplanted heart, lung, liver, and kidney in its earliest stage.

In a further aspect of the medical application of the present invention, the foregoing optical systems and methods may be applied to assess absolute properties of the substances included in the physiological medium. Examples of such substances may include, but not limited to, concentrations (or their ratios) of blood, lipids, cytochromes, water, and/or other chromophores in the medium.

The foregoing systems and methods of the present invention may be employed for various applications, e.g., non-invasively disposed on the medium or, alternatively, to be invasively disposed on an internal medium.

As used herein, a "hemoglobin" or "hemoglobins" refer to oxygenated hemoglobin and/or deoxygenated hemoglobin. In addition, the "hemoglobin," "hemoglobins," and/or "values of hemoglobins" represent properties of such "hemoglobins." Examples of such properties may include, but not limited to, amount or concentration thereof, total amount or total concentration thereof which corresponds to the sum of each amount or concentration of the oxygenated and deoxygenated hemoglobins, respectively.

A "chromophore" refers to any substance in a physiological medium optically interacting with photons or electromagnetic waves transmitting therethrough. Chromophore generally includes solvents of a physiological medium, solutes dissolved in such a medium, and/or other substances included in the medium. Specific examples of such chromophores may include, without limitation, cytochromes, enzymes, hormones, neurotransmitters, chemo- or chemical transmitters, proteins, cholesterols, apoproteins, lipids, carbohydrates, cytosols, cytosomes, blood cells, water, hemoglobins, and other optical materials present in animal or human cells, tissues or body fluid. Chromophores also include extra-cellular substances which may be injected into the medium for therapeutic and/or imaging purposes and may interact with electromagnetic waves. Such chromophores may include, without limitation, dyes, contrast agents, and other image-enhancing agents, each of which may exhibit optical interaction with electromagnetic waves having wavelengths in a specific range.

"Electromagnetic waves" as used herein generally refer to acoustic or sound waves, near-infrared rays, infrared rays, visible light rays, ultraviolet rays, lasers, and/or rays of photons.

"Property" of the chromophores may mean intensive or extensive property thereof. Examples of such intensive property may include, but not limited to concentration of the chromophore, a sum of such concentrations, and a ratio thereof. Examples of extensive property may include, without limitation, volume, mass, weight, volumetric flow rate, and mass flow rate of the chromophores.

The term "value" is an absolute value of the chromophore property. The term "value" may also refer to a relative value representing spatial or temporal changes in the property of the chromophores including deoxygenated and oxygenated hemoglobins.

Unless otherwise defined, all technical and scientific terms used herein have the same meaning as commonly understood and/or used by one of ordinary skill in the art to which this invention belongs. Although methods and materials similar or equivalent to those described herein can be applied and/or used in the practice of or testing the present invention, suitable methods and materials are described below. All publications, patent applications, patents, and other references mentioned herein are incorporated by reference in their entirety. In case of conflict, the present application, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Figure 1:
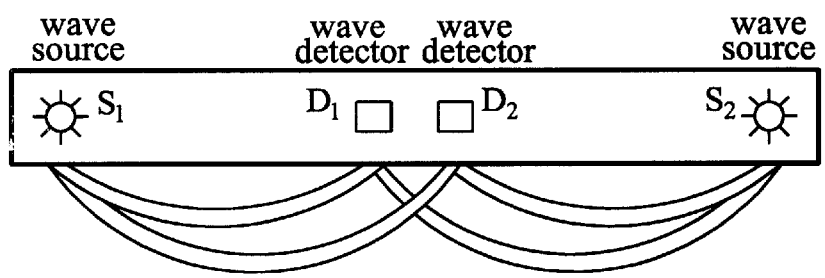
FIG. 1 is a schematic diagram of a sample optical system having two wave sources and two wave detectors having identical near-distances and far-distances according to the present invention.

The present invention relates to optical systems and methods thereof for determining absolute values of properties and/or conditions of a physiological medium. In particular, the following description provides various embodiments of optical systems and/or methods for determining the absolute values of concentrations of the hemoglobins (both of deoxy- and oxy-hemoglobin) and oxygen saturation (a ratio of oxy-hemoglobin concentration to total hemoglobin concentration which is a sum of the concentrations of deoxy-hemoglobin and oxy-hemoglobin) in a physiological medium. For these purposes, the following description provides novel methods for solving Beer-Lambert equations, generalized photon diffusion equations, and/or modified versions thereof. In addition, the description discloses various embodiments of optical imaging systems incorporating such methods. It is appreciated that the following methods and systems based thereon may be applied to determine absolute values of concentrations, their ratios, and/or volumes of other chromophores of the tissues and cells of the physiological medium.

In one aspect of the invention, a novel method is provided to solve the modified Beer-Lambert equation and/or the photon diffusion equation applied to an optical system including a source module and a detector module. The source module and detector module generally include, respectively, at least one wave source and at least one wave detector. However, it is generally preferred that the source and detector modules include at least two wave sources and two wave detectors, respectively.

As described hereinabove, equation (1) is the generalized governing equation for describing migration of photons or propagation of electromagnetic waves in a medium:

$$I = \alpha \cdot \beta \cdot \gamma \cdot I_o \cdot e^{[-B \cdot L \cdot \delta \cdot \Sigma_i(\varepsilon_i C_i) + \sigma]} \tag{1}$$

It is appreciated that the system parameters "$\gamma$" and "$\delta$" may have the value of 1.0 and "$\sigma$" may be 0.0. One simplified version of equation (1) may be obtained when the parameters "$\gamma$" and "$\delta$" are approximated as a unity:

$$I = \alpha \cdot \beta \cdot I_o \cdot e^{[-B \cdot L \Sigma_i(\varepsilon_i C_i) + \sigma]} \tag{3a}$$

The conventional "photon diffusion equation" has the same form as equation (3a):

$$I = S \cdot D \cdot I_o \cdot e^{[-B \cdot L \Sigma_i(\varepsilon_i C_i) + A]} \tag{3b}$$

where "S" corresponds to "$\alpha$" of equation (3a) and generally accounts for characteristics of the wave source such as irradiation power and geometric configuration thereof, mode of optical coupling between the wave source and medium, and/or associated optical coupling loss therebetween, "D" corresponds to "$\beta$" of equation (3a) and generally accounts for characteristics of the wave detector such as detection sensitivity and range, mode of optical coupling between the wave detector and medium, and/or the associated coupling loss, and "A" corresponds to "$\delta$" of equation (3a) which may be either a proportionality constant or a parameter associated with the wave source, wave detector, and/or medium. It is again noted that both "$I_o$" and "I" are functions of time only and preferably independent of frequency-domain frequency-domain parameters such as frequency and phase angle of such waves. It is also appreciated that the wave sources and detectors preferably operate in the CWS mode, i.e., the wave sources irradiate non-impulsive electromagnetic waves which have at least substantially identical amplitude over a measurable period. Therefore, the most preferred profile of the electromagnetic waves irradiated by the wave sources is a step-function (i.e., $I_o u(t)$) of which the characteristics are determined solely by their intensity (i.e., $I_o$) but not by the frequency-domain parameters. However, as long as the irradiated waves are non-impulsive, such waves can take the form of a single step (e.g., $I_o u(t)-I_o u(t-t_0)$, where $t_0$ represents a duration longer than a temporal sensitivity threshold of the wave detector. In the alternative, the irradiated waves may be a step-train comprised of a series of steps which have at least substantially identical amplitudes.

For illustration purposes, an exemplary optical system may include, e.g., two wave sources (S1 and S2) each emitting electromagnetic waves of wavelength $\lambda_1$ and two wave detectors (D1 and D2) arranged to detect at least a portion of such electromagnetic waves. Applying the photon diffusion equation (3b) to each pair of the wave sources and detectors of the exemplary optical system yields the following set of equations:

$$I_{S_1D_1}^{\lambda_1} = I_{S_1}^{\lambda_1} S_1 D_1 e^{-B_{S_1D_1}\left(\sum_i \varepsilon_i^{\lambda_1} C_i\right) L_{S_1D_1} + A} \tag{4a}$$

$$I_{S_1D_2}^{\lambda_1} = I_{S_1}^{\lambda_1} S_1 D_2 e^{-B_{S_1D_2}\left(\sum_i \varepsilon_i^{\lambda_1} C_i\right) L_{S_1D_2} + A} \tag{4b}$$

$$I_{S_2D_1}^{\lambda_1} = I_{S_2}^{\lambda_1} S_2 D_1 e^{-B_{S_2D_1}\left(\sum_i \varepsilon_i^{\lambda_2} C_i\right) L_{S_2D_1} + A} \tag{4c}$$

$$I_{S_2D_2}^{\lambda_1} = I_{S_2}^{\lambda_1} S_2 D_2 e^{-B_{S_2D_2}\left(\sum_i \varepsilon_i^{\lambda_1} C_i\right) L_{S_2D_2} + A} \tag{4d}$$

where the superscript $\lambda_1$ denotes that various variables and parameters are determined at the wavelength of $\lambda_1$.

A simple mathematical operation may eliminate at least one system parameter from the equations (4a) to (4d). For example, the source coupling factors such as $S_1$ and $S_2$ may be canceled therefrom by taking the first ratio of the equation (4a) to (4b) and by taking the fourth ratio of the equation (4d) to (4c). Logarithms of the first and second ratios are then taken to yield what are conventionally termed as "optical densities" (i.e., $OD_1^{\lambda_1}$ is defined as a logarithm of $I_{S_1D_1}^{\lambda_1}/I_{S_1D_2}^{\lambda_1}$ and $OD_2^{\lambda_2}$ defined as a logarithm of $I_{S_2D_2}^{\lambda_1}/I_{S_2D_1}^{\lambda_1}$):

$$OD_1^{\lambda_1} = \ln \frac{I_{S_1D_1}^{\lambda_1}}{I_{S_1D_2}^{\lambda_1}} = \ln \frac{D_1}{D_2} + (B_{S_1D_2}^{\lambda_1} L_{S_1D_2} - B_{S_1D_1}^{\lambda_1} L_{S_1D_1}) \sum_i \varepsilon_i^{\lambda_1} C_i \tag{5a}$$

$$OD_2^{\lambda_1} = \ln \frac{I_{S_2D_2}^{\lambda_1}}{I_{S_2D_1}^{\lambda_1}} = \ln \frac{D_2}{D_1} + (B_{S_2D_1}^{\lambda_1} L_{S_2D_1} - B_{S_2D_2}^{\lambda_1} L_{S_2D_2}) \sum_i \varepsilon_i^{\lambda_1} C_i \tag{5b}$$

It is appreciated that the optical densities are generally insensitive to exact modes of optical coupling between the wave source and the physiological medium. It is further appreciated that such optical densities solely depend on the intensities of the detected electromagnetic waves. Therefore, the optical densities are functions of time only and generally are independent of or at least substantially insensitive to the frequency-domain parameters.

Other system parameters may also be eliminated through reformulating the above equations (5a) and (5b). For example, the terms including the detector coupling factors, $D_1$ and $D_2$, may be canceled by adding equation (5a) to (5b):

$$OD^{\lambda_1} = OD_1^{\lambda_1} + OD_2^{\lambda_2} = F^{\lambda_1} \sum_i \varepsilon_i^{\lambda_1} C_i \tag{6a}$$

where $F^{\lambda_1}=(B_{S_1D_2}^{\lambda_1}L_{S_1D_2}-B_{S_1D_1}^{\lambda_1}L_{S_1D_1})+(B_{S_2D_1}^{\lambda_1}L_{S_2D_1}-B_{S_2D_2}^{\lambda_1}L_{S_2D_2})$. (6b)

As manifest in equation (6b), $F^{\lambda_1}$ is primarily determined by configurations of the wave sources and detectors (i.e., "L's" which are predominantly "geometry-dependent" and which account for distances between each pair of a wave source and a wave detector) as well as the path length factors (i.e., "B's" which are predominantly "medium-dependent" and which are determined by the optical properties of the physiological medium and/or electromagnetic waves).

Equations (6a) and (6b) may be applied to the physiological medium in order to obtain quantitative physiological information such as concentrations of the chromophores and/or their ratios. Numerous substances contained or suspended in the medium may be capable of interacting or interfering with photons or electromagnetic waves impinging or propagating therethrough. However, in many physiological media, hemoglobins such as deoxygenated and deoxy-hemoglobin (Hb) and oxygenated or oxy-hemoglobin (HbO) are the chromophores of the most physiological interests. Applying equations (6a) and (6b) to such physiological medium yields:

$$\frac{OD^{\lambda_1}}{F^{\lambda_1}} = \sum_i \varepsilon_i^{\lambda_1} C_i = \varepsilon_{Hb}^{\lambda_1}[Hb] + \varepsilon_{HbO}^{\lambda_1}[HbO] \tag{7a}$$

where [Hb] and [HbO] respectively represent concentrations of Hb and HbO.

By arranging the wave sources, S1 and S2, or additional wave sources, e.g., S3 and S4, to irradiate a second set of electromagnetic waves having a wavelength $\lambda_2$ which is different from the wavelength $\lambda_1$, a companion equation of the equation (7a) is obtained as follows:

$$\frac{OD^{\lambda_2}}{F^{\lambda_2}} = \sum_i \varepsilon_i^{\lambda_2} C_i = \varepsilon_{Hb}^{\lambda_2}[Hb] + \varepsilon_{HbO}^{\lambda_2}[HbO] \tag{7b}$$

Accordingly, mathematical expressions of two system variables [Hb] and [HbO] can be readily derived from an algebraic system of equations (7a) and (7b) as follows:

$$[Hb] = \frac{\varepsilon_{HbO}^{\lambda_2} \frac{OD^{\lambda_1}}{F^{\lambda_1}} - \varepsilon_{HbO}^{\lambda_1} \frac{OD^{\lambda_2}}{F^{\lambda_2}}}{\varepsilon_{Hb}^{\lambda_1}\varepsilon_{HbO}^{\lambda_2} - \varepsilon_{Hb}^{\lambda_2}\varepsilon_{HbO}^{\lambda_1}} \tag{8a}$$

$$[HbO] = \frac{\varepsilon_{Hb}^{\lambda_1} \frac{OD^{\lambda_2}}{F^{\lambda_2}} - \varepsilon_{Hb}^{\lambda_2} \frac{OD^{\lambda_1}}{F^{\lambda_1}}}{\varepsilon_{Hb}^{\lambda_1}\varepsilon_{HbO}^{\lambda_2} - \varepsilon_{Hb}^{\lambda_2}\varepsilon_{HbO}^{\lambda_1}} \tag{8b}$$

where $F^{\lambda_1}=(B_{S_1D_2}^{\lambda_1}L_{S_1D_2}-B_{S_1D_1}^{\lambda_1}L_{S_1D_1})+(B_{S_2D_1}^{\lambda_1}L_{S_2D_1}-B_{S_2D_2}L_{S_2D_2})$. (8c)

and $F^{\lambda_1}=(B_{S_1D_2}^{\lambda_1}L_{S_1D_2}-B_{S_1D_1}^{\lambda_1}L_{S_1D_1})+(B_{S_2D_1}^{\lambda_1}L_{S_2D_1}-B_{S_2D_2}L_{S_2D_2})$. (8d)

Expressions of other physiological properties or indices may also be derived from the above equations. For example, oxygen saturation ($SO_2$) is a frequently used index for diagnosis of ischemic conditions and generally defined as a ratio of concentration of oxy-hemoglobin to total concentration of hemoglobins (i.e., [HbT]=[Hb]+[HbO]):

$$SO_2 = \frac{[HbO]}{[HbT]} = \frac{[HbO]}{[Hb]+[HbO]} \qquad (9a)$$

Incorporating equations (8a) and (8b) to equation (9a) yields a following formula for the oxygen saturation as a function of the extinction coefficients ($\epsilon$'s), optical densities (OD's), and medium/geometry-dependent factors, $F^{\lambda_1}$ and $F^{\lambda_2}$:

$$SO_2 = \frac{\epsilon_{Hb}^{\lambda_1}\frac{OD^{\lambda_2}}{OD^{\lambda_1}}\frac{F^{\lambda_1}}{F^{\lambda_2}} - \epsilon_{Hb}^{\lambda_2}}{\left(\epsilon_{Hb}^{\lambda_1}-\epsilon_{HbO}^{\lambda_1}\right)\frac{OD^{\lambda_2}}{OD^{\lambda_1}}\frac{F^{\lambda_1}}{F^{\lambda_2}} + \left(\epsilon_{HbO}^{\lambda_2}-\epsilon_{Hb}^{\lambda_2}\right)} \qquad (9b)$$

The extinction coefficients of the oxy- and deoxy-hemoglobins measured at different wavelengths $\lambda_1$ and $\lambda_2$ can be obtained from the literature or from a separate measurement. As will be explained in greater below, the medium/geometry-dependent factors $F^{\lambda_1}$ and $F^{\lambda_2}$ can also be obtained empirically, semi-empirically or theoretically. Therefore, the absolute values of the concentrations of the deoxygenated and oxygenated hemoglobins, [Hb] and [HbO] respectively, can be obtained by plugging into the equations known values of extinction coefficients ($\epsilon$'s), experimentally measured optical densities (OD's), and readily obtainable values of medium/geometry-dependent factors, $F^{\lambda_1}$ and $F^{\lambda_2}$. In addition, the absolute value of the tissue oxygen saturation ($SO_2$) can also be directly determined from the absolute values of [Hb] and [HbO]. In short, the optical systems and methods of the present invention allow the determination of the absolute value of the hemoglobin (and other chromophores) concentrations and/or their ratios solely by measuring the intensities of the electromagnetic waves irradiated by the wave sources and those of the electromagnetic waves detected by the wave detectors.

It is noted that estimation of $F^{\lambda_1}$ and $F^{\lambda_2}$ is not straightforward because the path length factors including such terms usually depend on specific types of the physiological medium as well as optical or energy characteristics of electromagnetic waves or photons. One way of estimating or approximating the values of $F^{\lambda_1}$ and $F^{\lambda_2}$ is to assume that $F^{\lambda_1}$, $F^{\lambda_2}$, or their ratio may only marginally depend on background optical properties and configurations of the wave sources and detectors. It is believed that these assumptions are fairly accurate in linear optical processes such as migration of photons or propagation of electromagnetic waves in the physiological media.

Once the correlations of the ratio of $F^{\lambda_1}$ to $F^{\lambda_2}$ with oxygen saturation is obtained for different physiological media by simply measuring the optical properties thereof, such correlations may be incorporated into equations (8a), (8b), and (9b), and the absolute values of [Hb], [HbO], and/or oxygen saturation may be obtained. In particular, a ratio of $F^{\lambda_1}$ to $F^{\lambda_1}$ may be approximated, e.g., as a polynomial of oxygen saturation as follows:

$$G = \frac{F^{\lambda_1}}{F^{\lambda_2}} = \sum_{i=0}^{\infty} a_j SO_2^j = a_0 + a_1 SO_2 + a_2 SO_2^2 + a_3 SO^3 + \dots \qquad (10)$$

where coefficients of each term (i.e., $\alpha_0, \alpha_1, \alpha_2, \alpha_3 \dots$) may be obtained by, e.g., theoretical derivation, semi-theoretical estimation or numerical method best-fitting experimental data obtained between the values of G and oxygen saturation. By incorporating the formula for G of equation (10) into equation (9b), the absolute value of the oxygen saturation may be obtained from known values of the extinction coefficients (i.e., "$\epsilon_i$'s") and experimentally measured optical densities (i.e., "OD's") as follows:

$$SO_2 = \frac{\epsilon_{Hb}^{\lambda_1}\frac{OD^{\lambda_2}}{OD^{\lambda_1}}\sum_{j=0}^{\infty} a_j SO_2^j - \epsilon_{Hb}^{\lambda_2}}{\left(\epsilon_{Hb}^{\lambda_1}-\epsilon_{HbO}^{\lambda_1}\right)\frac{OD^{\lambda_2}}{OD^{\lambda_1}}\sum_{j=0}^{\infty} a_j SO_2^j + \left(\epsilon_{HbO}^{\lambda_2}-\epsilon_{Hb}^{\lambda_2}\right)} \qquad (11)$$

By plugging into equation (11) the values of extinction coefficients ($\epsilon$'s), coefficients of the correlation such as equation (10), and experimentally measured optical densities (OD's), Equation (11) can be generally solved numerically. However, an analytical expression for the oxygen saturation may also be obtained when only a few first terms of the polynomials are adopted so as to approximate G, i.e., the ratio of $F^{\lambda_1}$ to $F^{\lambda_2}$. Other methods may also be applied to approximate G. For example, G may be estimated as a function of [Hb] and/or [HbO], although it is noted that the accuracy of this estimation may depend on the one-to-one correspondence between G and [Hb] and/or [HbO]. Alternatively, G may further be approximated as a constant as well. This approximation may be a reasonable assumption when $F^{\lambda_1}$ and $F^{\lambda_2}$ are relatively constant or tend to vary in proportion to each other according to different values of [Hb], [HbO], and/or oxygen saturation. In the alternative, the value of "$L_{mn}$" may be varied by manipulating geometric configuration of the wave sources and detectors so as to render G stay constant or vary in a pre-determined manner.

Similarly, each of $F^{\lambda_1}$ and $F^{\lambda_2}$ may be approximated as a function of [Hb], [HbO], and/or oxygen saturation. In the alternative, $F^{80\ 1}$ and $F^{\lambda_2}$ may also be assigned specific values which may best approximate the optical system and/or the physiological medium of interest. By taking the simplest approach of approximating $F^{\lambda_1}$ and $F^{\lambda_2}$ to be a unity, the absolute values of [Hb], [HbO], and oxygen saturation may be obtained as follows:

$$[Hb] = \frac{\epsilon_{HbO}^{\lambda_2}OD^{\lambda_1} - \epsilon_{HbO}^{\lambda_1}OD^{\lambda_2}}{\epsilon_{Hb}^{\lambda_1}\epsilon_{HbO}^{\lambda_2} - \epsilon_{Hb}^{\lambda_2}\epsilon_{HbO}^{\lambda_1}} \qquad (12a)$$

$$[HbO] = \frac{\epsilon_{Hb}^{\lambda_1}OD^{\lambda_2} - \epsilon_{Hb}^{\lambda_2}OD^{\lambda_1}}{\epsilon_{Hb}^{\lambda_1}\epsilon_{HbO}^{\lambda_2} - \epsilon_{Hb}^{\lambda_2}\epsilon_{HbO}^{\lambda_1}} \qquad (12b)$$

$$SO_2 = \frac{\epsilon_{Hb}^{\lambda_1}\frac{OD^{\lambda_2}}{OD^{\lambda_1}} - \epsilon_{Hb}^{\lambda_2}}{\left(\epsilon_{Hb}^{\lambda_1}-\epsilon_{HbO}^{\lambda_1}\right)\frac{OD^{\lambda_2}}{OD^{\lambda_1}} + \left(\epsilon_{HbO}^{\lambda_2}-\epsilon_{Hb}^{\lambda_2}\right)} \qquad (12c)$$

In this embodiment, oxygen saturation ($SO_2$) can be determined solely by the known values of the extinction coefficients ($\epsilon$'s) and experimentally measured optical densities (OD's).

It is noted that [Hb], [HbO], and/or oxygen saturation obtained from the equations (12a) to (12c) (and/or other approximation methods described hereinabove) may be less accurate than those obtained from equations (8a), (8b), and (9b). Nevertheless, as long as the foregoing assumptions hold valid, one-to-one correlations may be expected between the true values of [Hb], [HbO], and oxygen saturation and those obtained from approximating equations (12a) to (12c). Such correlations may be determined once the optical properties of the physiological medium are known. For example, extinction coefficients, absorption coefficients, and/or scattering coefficients of the physiological medium (or those of the chromophores) may be determined for [HbT] and oxygen saturation. With known optical properties, oxygen saturation may be estimated at different levels of [HbT] through simulations of the diffusion equations and/or through experiments. Equations (12a) and (12b) may then be used to back-calculate [HbT], and a correction function can be calculated which correlates the calculated [HbT] with the true [HbT]. Similar or identical approach may be applied to calculate correction functions for [Hb] and/or [HbO] as well. It is noted that these methods may be applied to different physiological media (e.g., different human or animal subjects) to assess different optical properties and, therefore, to obtain different correction functions.

It is appreciated that the foregoing methods are applicable to any optical system and physiological media where migration of photons or propagation of electromagnetic waves may be reasonably described by the generalized governing equation (1). It should be noted that the parameter eliminating step of the foregoing methods may be applicable regardless of the specific numerical values assigned to the parameters "γ" and "δ". For example, γ can be eliminated by taking ratios of equation (4a) to (4b) and equation (4d) to (4c), and 67 can be eliminated by taking the ratio of $F^{\lambda_1}$ to $F^{\lambda_2}$. In addition, the foregoing method may also be readily applicable to any modified versions of the governing equation (1) where the optical interaction or interference of the medium is described by the absorption coefficient, scattering coefficients, and/or reduced scattering coefficient of the chromophores and/or the medium. For example, by assigning an adequate value and unit to parameter "γ," such modified equations can be converted into equations substantially similar or identical to the governing equation (1). Therefore, it is manifest that the foregoing methods may be deemed universal for solving the governing equation (1) for the chromophore concentrations and/or their ratios.

It is further appreciated that the absolute values of the chromophore concentrations (or their ratios) may be obtained by variations of the foregoing methods. For example, the detector coupling factors, $D_1$ and $D_2$, may first be eliminated from equations (4a) to (4d) by taking the third ratio of the equation (4a) to (4c) and the fourth ratio of the equation (4d) to (4b) as follows:

$$OD_3^{\lambda_1} = \ln \frac{I_{S1D1}^{\lambda_1}}{I_{S2D1}^{\lambda_1}} \tag{5c}$$

$$= \ln \frac{I_{S1}^{\lambda_1}}{I_{S2}^{\lambda_1}} + \ln \frac{S_1}{S_2} + \left(B_{S2D1}^{\lambda_1} L_{S2D1} - B_{S1D1}^{\lambda_1} L_{S1D1}\right) \sum_i \varepsilon_i^{\lambda_1} C_i$$

$$OD_4^{\lambda_1} = \ln \frac{I_{S2D2}^{\lambda_1}}{I_{S1D2}^{\lambda_1}} \tag{5d}$$

$$= \ln \frac{I_{S2}^{\lambda_1}}{I_{S1}^{\lambda_1}} + \ln \frac{S_2}{S_1} + \left(B_{S1D2}^{\lambda_1} L_{S1D2} - B_{S2D2}^{\lambda_1} L_{S2D2}\right) \sum_i \varepsilon_i^{\lambda_1} C_i$$

Similar to equations (5a) and (5b), this variational method yields optical densities $OD_3^{\lambda_1}$ and $OD_4^{\lambda_1}$ which are substantially insensitive to the coupling mode between the wave detector and the medium. By adding equation (5c) to (5d), the logarithmic ratios (i.e., one ratio of intensities of the electromagnetic waves irradiated by the wave sources and another ratio of the source coupling factors, $S_1$ and $S_2$) also cancel each other, yielding:

$$OD_{34}^{\lambda_1} = OD_3^{\lambda_1} + OD_4^{\lambda_1} = F_{34}^{\lambda_1} \sum_i \varepsilon_i^{\lambda_1} C_i \tag{6c}$$

where $F_{34}^{\lambda_1} = (B_{S2D1}^{\lambda_1} L_{S2D1} - B_{S1D1}^{\lambda_1} L_{S1D1}) + (B_{S1D2}^{\lambda_1} L_{S1D2} - B_{S2D2}^{\lambda_1} L_{S2D2})$. (6d)

By applying equations (6c) and (6d) to the physiological medium including oxy- and deoxy-hemoglobins, following equation (7c) is obtained:

$$\frac{OD_{34}^{\lambda_1}}{F_{34}^{\lambda_1}} = \sum_i \varepsilon_i^{\lambda_1} C_i = \varepsilon_{Hb}^{\lambda_1}[Hb] + \varepsilon_{HbO}^{\lambda_1}[HbO] \tag{7c}$$

Similarly, a companion equation of equation (7c) may be obtained by applying the second set of electromagnetic waves having a wave length $\lambda_2$:

$$\frac{OD_{34}^{\lambda_2}}{F_{34}^{\lambda_2}} = \sum_i \varepsilon_i^{\lambda_2} C_i = \varepsilon_{Hb}^{\lambda_2}[Hb] + \varepsilon_{HbO}^{\lambda_2}[HbO] \tag{7d}$$

Thus, by solving equations (7c) and (7d), mathematical expressions of two system variables [Hb] and [HbO] can be obtained as follows:

$$[Hb] = \frac{\varepsilon_{HbO}^{\lambda_2} \frac{OD_{34}^{\lambda_1}}{F_{34}^{\lambda_1}} - \varepsilon_{HbO}^{\lambda_1} \frac{OD_{34}^{\lambda_2}}{F_{34}^{\lambda_2}}}{\varepsilon_{Hb}^{\lambda_1} \varepsilon_{HbO}^{\lambda_2} - \varepsilon_{Hb}^{\lambda_2} \varepsilon_{HbO}^{\lambda_1}} \tag{8e}$$

$$[HbO] = \frac{\varepsilon_{Hb}^{\lambda_1} \frac{OD_{34}^{\lambda_2}}{F_{34}^{\lambda_2}} - \varepsilon_{Hb}^{\lambda_2} \frac{OD_{34}^{\lambda_1}}{F_{34}^{\lambda_1}}}{\varepsilon_{Hb}^{\lambda_1} \varepsilon_{HbO}^{\lambda_2} - \varepsilon_{Hb}^{\lambda_2} \varepsilon_{HbO}^{\lambda_1}} \tag{8f}$$

where $F_{34}^{\lambda_1} = (B_{S2D1}^{\lambda_1} L_{S2D1} - B_{S1D1}^{\lambda_1} L_{S1D1}) + (B_{S1D2}^{\lambda_1} L_{S1D2} - B_{S2D2}^{\lambda_1} L_{S2D2})$. (8g)

and $F_{34}^{\lambda_2} = (B_{S2D1}^{\lambda_2} L_{S2D1} - B_{S1D1}^{\lambda_2} L_{S1D1}) + (B_{S1D2}^{\lambda_2} L_{S1D2} - B_{S2D2}^{\lambda_2} L_{S2D2})$. (8h)

The oxygen saturation may then be expressed as:

$$SO_2 = \frac{\varepsilon_{Hb}^{\lambda_1} \frac{OD_{34}^{\lambda_2}}{OD_{34}^{\lambda_1}} \frac{F_{34}^{\lambda_1}}{F_{34}^{\lambda_2}} - \varepsilon_{Hb}^{\lambda_2}}{(\varepsilon_{Hb}^{\lambda_1} - \varepsilon_{HbO}^{\lambda_1}) \frac{OD_{34}^{\lambda_2}}{OD_{34}^{\lambda_1}} \frac{F_{34}^{\lambda_1}}{F_{34}^{\lambda_2}} + (\varepsilon_{HbO}^{\lambda_2} - \varepsilon_{Hb}^{\lambda_2})} \tag{9c}$$

Other variations of the foregoing methods leading to equations (9b) and (9c) may also be used as long as they are designed to eliminate system parameters and to ultimately express [Hb], [HbO], and/or oxygen saturation in terms of known or measurable system variables or parameters such as, e.g., the experimentally measured optical densities, known values of the extinction coefficients, and/or other geometry-dependent parameters readily determined by the actual geometry of the source-detector arrangement.

It is further appreciated that the foregoing method of the present invention allows the wave sources to irradiate multiple sets of electromagnetic waves which have different wave characteristics through various different embodiments.

The simplest arrangement may be to provide two wave sources (such as S1 and S2), where each source is designated to irradiate the electromagnetic waves having different wavelengths, phase angles, and/or harmonics.

For example, the optical monitoring and/or imaging systems operating in the CWS mode include the wave sources preferably irradiating non-impulsive and non-phase-modulated electromagnetic waves which have at least substantially identical amplitudes over a minimal measurable period. Similarly, the wave detectors of CWS systems only perform the intensity measurement of the electromagnetic waves on a continuous basis. It is appreciated that such intensity measurement may also be performed on an intermittent basis as long as the wave detector can detect the waves for a period of time sufficient to detect the intensities thereof. Thus, the wave sources of the CWS systems do not have to irradiate continuous electromagnetic waves.

Alternatively, each wave source may also be arranged to irradiate substantially identical signal waves which are, however, superimposed on different carrier waves. In yet another alternative, a single or each wave source may be arranged to irradiate multiple sets of electromagnetic waves intermittently, sequentially or simultaneously as long as different sets of electromagnetic waves can be identifiable by one or more wave detectors. Similar arrangements may also be applied to the wave detectors as well. For example, two wave detectors (D1 and D2) may be provided where each detector is designated to detect only a single set of electromagnetic waves. Alternatively, a single or each wave detector may detect multiple sets of electromagnetic waves with different wave characteristics on an intermittent, sequential or simultaneous mode. Because the foregoing systems and methods of the present invention allow these various arrangements, they can be readily incorporated into any conventional spectroscopy such as the TRS, PMS, and CWS.

In another aspect of the invention, an over-determined numerical method is provided to solve the modified Beer-Lambert equation and/or the photon diffusion equation applied to an optical system including a source module and a detector module, where at least one of the source module and detector module may be arranged to irradiate or detect more than two sets of electromagnetic waves. By arranging an optical system to provide "more equations" than "the number of system variables" of interest, resulting extra equations may be utilized for other purposes, e.g., (i) to enhance the accuracy of estimated values of system variables (e.g., chromophore concentrations or their ratios), (ii) to determine system parameters (e.g., "$\alpha_m$," "$\beta_n$," "$\gamma$," "$B_{mn}$," "$L_{mn}$," "$\delta$," "$\epsilon_i$," "$\sigma$" or other parameters such as absorption and scattering coefficients of the medium and/or chromophores) or (iii) to provide correlations between the medium- and/or geometry-dependent parameters of the equations (1) or (3b) and the system variable(s) and/or other system parameters.

In the first embodiment, the extra equations may be used to obtain multiple values of the chromophore concentrations (and/or their ratios). It is expected that discrepancies may exist, at least to some extent, among the estimated values of the concentrations (and/or their ratios). Such discrepancies may be attributed to inherent idiosyncracy of each pair of the wave sources and detectors. Alternatively, the discrepancies may also arise from a non-homogeneous medium having regional variations in optical properties. One way of taking advantage of different values of the concentrations of the chromophores (and/or their ratios) may be to average such values to obtain an arithmetic, geometric or logarithmic average to reduce random or systematic errors and to improve accuracy. Alternatively, each measured value may be weight-averaged by an appropriate weight function which may account for, e.g., geometric configuration of the wave source and detector assembly.

In the second embodiment, correlations between the medium- and/or geometry-dependent parameters of the equations (1) or (3b) and the chromophores concentrations (or their ratios) may be obtained from those extra equations. For example, when G (i.e., the ratio of $F^{\lambda_1}$ to $F^{\lambda_2}$) is approximated as a polynomial of oxygen saturation according to the equation (10), each coefficient of the polynomial may be assigned an initial value which is then improved by iterative techniques employing a conventional numerical fitting method. In addition, the extra equations may also be used to find the correction functions between the approximated and true values of oxygen saturation, [Hb], and/or [HbO].

Furthermore, the extra equations may also be used to estimate system parameters (e.g., "$\alpha_m$," "$\beta_n$," "$\gamma$," "$B_{mn}$," "$L_{mn}$," "$\delta$," "$\epsilon_i$," "$\sigma$," and/or other system parameters such as absorption coefficients and/or scattering coefficients of the medium and/or chromophores). For example, a forward numerical scheme may be used to estimate absorption and reduced scattering coefficients of the physiological medium and/or chromophores included therein. As described hereinabove, migration of photons and propagation of electromagnetic waves in the medium can be described by the diffusion or transport equation. Assuming that the medium is semi-infinite and homogeneous, following equation may describe an intensity of electromagnetic waves detected by a j-th detector:

$$I_{ij}^{\lambda} = S_i^{\lambda} D_j^{\lambda} \phi(r_i, r_j, \mu_a, \mu_s) \tag{13}$$

where $S_i$ generally denotes a source coupling parameter accounting for, e.g., characteristics of an i-th wave source such as irradiation power and configuration thereof, mode of optical coupling between the i-th wave source and medium, and/or optical coupling loss therebetween, and where $D_j$ is a detector coupling factor generally accounting for characteristics of a j-th wave detector, mode of optical coupling between the j-th wave detector and medium, and the associated coupling loss therebetween.

A symbol "$\phi$" represents a forward numerical model simulating measurement for a given pair of a wave source and detector. Parameters "$\mu_a$" and "$\mu_s$" represent, respectively, an absorption coefficient and (reduced) scattering coefficient. When the optical system includes, e.g., a total number of $N_S$ wave sources and $N_D$ wave detectors, equation (13) can be expressed in a matrix form as follows:

$$\begin{bmatrix} I_{11} & \cdots & I_{1,N_D} \\ \vdots & \ddots & \vdots \\ I_{N_S,1} & \cdots & I_{N_S,N_S} \end{bmatrix} = \tag{14}$$

$$\begin{bmatrix} S_1^{\lambda} D_1^{\lambda} \phi(r_1, r_1, \mu_a, \mu_s') & \cdots & S_1^{\lambda} D_{N_D}^{\lambda} \phi(r_1, r_{N_D}, \mu_a, \mu_s') \\ \vdots & \ddots & \vdots \\ S_{N_S}^{\lambda} D_1^{\lambda} \phi(r_{N_S}, r_1, \mu_a, \mu_s') & \cdots & S_{N_S}^{\lambda} D_{N_D}^{\lambda} \phi(r_{N_S}, r_{N_D}, \mu_a, \mu_s') \end{bmatrix}$$

It is appreciated that all system variables, $I_{ij}(i=1, \ldots N_S$ and $j=1, \ldots N_S)$, are functions of time and preferably independent of or at least substantially insensitive to the frequency-domain parameters. Each side of the equation (14) is divided by the first column of each matrix:

$$\begin{bmatrix} 1 & \cdots & \frac{I_{1,N_D}}{I_{1,1}} \\ \vdots & \ddots & \vdots \\ 1 & \cdots & \frac{I_{N_S,N_D}}{I_{N_S,1}} \end{bmatrix} = \begin{bmatrix} 1 & \cdots & \frac{D_{N_D}^\lambda \cdot \phi(r_1, r_1, \mu_a, \mu_s')}{D_1^\lambda \cdot \phi(r_1, r_1, \mu_a, \mu_s')} \\ \vdots & \ddots & \vdots \\ 1 & \cdots & \frac{D_{N_D}^\lambda \cdot \phi(r_{N_S}, r_{N_D}, \mu_a, \mu_s')}{D_1^\lambda \cdot \phi(r_{N_S}, r_1, \mu_a, \mu_s')} \end{bmatrix} \quad (15)$$

Each row of the matrices of equation (15) is then divided by the first row of each matrix to yield matrices A and B:

$$A \equiv \begin{bmatrix} 1 & \cdots & 1 \\ \vdots & \ddots & \vdots \\ 1 & \cdots & \frac{I_{N_S, N_D}}{I_{N_S, 1}} \end{bmatrix} = \quad (16)$$

$$\begin{bmatrix} 1 & \cdots & 1 \\ \vdots & \ddots & \vdots \\ 1 & \cdots & \frac{\phi(r_{N_S}, r_{N_D}, \mu_a, \mu_s') \cdot \phi(r_1, r_{N_D}, \mu_a, \mu_s')}{\phi(r_{N_S}, r_1, \mu_a, \mu_s') \cdot \phi(r_1, r_1, \mu_a, \mu_s')} \end{bmatrix} \equiv B$$

As manifest in equation (16), both of the matrices A and B are functions of the absorption and reduced scattering coefficients and do not depend on the source- and detector-coupling parameters such as $S_i$ and $D_j$. Accordingly, by minimizing the difference between A and B (i.e., $\|A-B\|$), the best estimates of the absorption coefficient and (reduced) scattering coefficient may be numerically obtained by conventional curve-fitting methods. After estimating the absorption and reduced scattering coefficients, [Hb], [HbO], and oxygen saturation may be obtained by the following set of formulae:

$$[Hb] = \frac{\varepsilon_{HbO}^{\lambda_2} \mu_a^{\lambda_1} - \varepsilon_{HbO}^{\lambda_1} \mu_a^{\lambda_2}}{\varepsilon_{Hb}^{\lambda_1} \varepsilon_{HbO}^{\lambda_2} - \varepsilon_{Hb}^{\lambda_2} \varepsilon_{HbO}^{\lambda_1}} \quad (17a)$$

$$[HbO] = \frac{\varepsilon_{Hb}^{\lambda_1} \mu_a^{\lambda_2} - \varepsilon_{Hb}^{\lambda_2} \mu_a^{\lambda_1}}{\varepsilon_{Hb}^{\lambda_1} \varepsilon_{HbO}^{\lambda_2} - \varepsilon_{Hb}^{\lambda_2} \varepsilon_{HbO}^{\lambda_1}} \quad (17b)$$

$$SO_2 = \frac{[HbO]}{[Hb] + [HbO]} \quad (17c)$$

$$= \frac{\varepsilon_{Hb}^{\lambda_1} \mu_a^{\lambda_2} - \varepsilon_{Hb}^{\lambda_2} \mu_a^{\lambda_1}}{\left(\varepsilon_{HbO}^{\lambda_2} \mu_a^{\lambda_1} - \varepsilon_{HbO}^{\lambda_1} \mu_a^{\lambda_2}\right) + \left(\varepsilon_{Hb}^{\lambda_1} \mu_a^{\lambda_2} - \varepsilon_{Hb}^{\lambda_2} \mu_a^{\lambda_1}\right)}$$

It is noted that the foregoing over-determined method may be applied to the optical systems with at least two wave sources and three wave detectors, at least three wave sources and two wave detectors, or three wave sources and three wave detectors. In the alternative, the over-determined method may equally be applied to the optical systems where a single or each wave source or detector has the capability of irradiating or detecting multiple sets of electromagnetic waves, respectively.

It is appreciated that the foregoing over-determined method may be incorporated into any conventional numerical schemes. For example, a forward, backward or hybrid model may be applied to determine, e.g., an extinction coefficient, absorption coefficient or scattering coefficient of the physiological medium (or the chromophores included therein). Such models may also be applied to estimate the absolute values of the concentrations of the chromophores (and/or ratios thereof). It is noted, however, that the results obtained by such numerical models generally include errors associated therewith. Such inherent errors may be minimized by employing numerical models with the error terms of the second or higher order. However, such models may have a major drawback of requiring rigorous numerical computations. Accordingly, the accuracy and efficiency of each numerical model must be considered in selecting an appropriate model.

In yet another aspect of the invention, an optical system is provided to solve a set of wave equations and to determine absolute values of the concentrations of the chromophores (and/or ratios thereof) contained or suspended in a physiological medium. An exemplary optical system may include a body, a source module including at least one wave source, a detector module having at least one wave detector, and a processing module. The source module is supported by the body, optically couples with the physiological medium, and irradiates into the medium at least two sets of electromagnetic waves having different wave characteristics. The detector module is also supported by the body, optically couples with the medium, and detects electromagnetic waves transmitted through the medium. The processing module operatively couples with the detector module, solves a set of multiple wave equations, and determines the absolute values of the chromophore concentrations and/or ratios thereof.

In general, the processing module includes an algorithm which is arranged to solve the foregoing equations (1) or (3b) or their modified versions. For example, one or more of the foregoing methods may be incorporated into hardware or software or implemented into a microprocessor. Accordingly, the absolute values of the chromophore concentrations (and/or their ratios) can be calculated from, e.g., experimentally measured intensity of the electromagnetic waves irradiated by the wave source, experimentally measured intensity of the electromagnetic waves detected by the wave detector, and at least one system parameter which may account for an optical interaction or interference between the electromagnetic waves and the medium. The algorithm of the processing module may include one or more functions or correlations expressing the medium- and/or geometry-dependent term(s) of the foregoing wave equations as a function of the chromophore concentrations (or their ratios). The algorithm of the processing module may be capable of executing the over-determined method described hereinabove. In addition, the processing module and algorithm thereof may be modified to operate in the TRS and PMS modes.

The source module may include at least one wave source and the detector module may include at least two wave detectors. Alternatively, the source module may include at least two wave sources while the detector module may include at least one wave detector. It is preferred, however, that the source and detector modules include, respectively, at least two wave sources and at least two wave detectors.

As described hereinabove, the foregoing methods of the present invention are rather insensitive to actual configuration of wave sources and detectors. Accordingly, the optical monitoring and imaging systems of the present invention may include any number of wave sources and/or detectors arranged in any arbitrary configuration. However, a few source-detector configurations may be preferred to obtain the absolute values of the chromophore concentrations (and/or their ratios) with better accuracy, reliability, and reproducibility.

In one exemplary embodiment, multiple wave sources and wave detectors may be arranged so that near-distances between each pair of the wave source and detector are at least substantially identical. For example, for the source module including a first and a second wave source and the detector module including a first and a second wave detector, a first near distance between the first wave source and the first wave detector may be arranged to be substantially similar to a second near-distance between the second wave source and the second wave detector. In addition, a first far-distance between the first wave source and the second wave detector may be arranged to be substantially similar to a second far-distance between the second wave source and the first wave detector. It is appreciated that such an embodiment is not necessary for every single pair of the wave sources and detectors. For example, when the source module has M wave sources and the detector module has N wave detectors (M and N are integers greater than 1), at least two of M wave sources and two of N wave detectors may be arranged so that a distance between an $M_1$-th wave source and an $N_1$-th detector is substantially similar to that between an $M_2$-th wave source and an $N_2$-th wave detector, and that a distance between the $M_1$-th wave source and the $N_2$-th wave detector is substantially similar to that between the $M_2$-th wave source and the $N_1$-th wave detector, where $M_1$ and $M_2$ are both integers between 1 and M, and where $N_1$ and $N_2$ are both integers between 1 and N.

Such an embodiment is typically realized by the wave sources and detectors arranged substantially symmetrically, e.g., those arranged substantially linearly along a straight line. FIG. 1 is a schematic diagram of a sample optical system having two wave sources and two wave detectors having identical near-distances and far-distances according to the present invention. It is first appreciated that the source-detector arrangement of FIG. 1 satisfies the identical near-distance and far-distance configuration. For example, the first near-distance between the wave source $S_1$ and detector $D_1$ is identical or substantially similar to the second near-distance between the wave source $S_2$ and detector $D_2$. In addition, the first far-distance between the wave source $S_1$ and detector $D_2$ is identical or substantially similar to the second far-distance between the wave source S2 and detector $D_1$. An advantage of satisfying such configurational limitation lies in the observation that electromagnetic waves are substantially uniformly transmitted, absorbed or scattered throughout the entire target area or target volume of the medium (refer to banana-shaped paths of the electromagnetic waves in the figure). Therefore, the photos or electromagnetic radiation uniformly covers all regions of the target area of the medium and, therefore, enhances the accuracy as well as reliability of the output signal (e.g., an improved signal-to-noise ratio) generated by the wave detector. As will be demonstrated in the following Examples, the foregoing linear arrangement of the wave sources and detectors has provided the absolute values of the concentrations of oxygenated and deoxygenated hemoglobins and oxygen saturation with great accuracies. It is also appreciated that not all wave sources and/or detectors have to be arranged linearly. For example, the wave sources and wave detectors may be arranged not linearly but substantially symmetrically with respect to a line of symmetry and/or a point of symmetry. As long as such symmetric configuration is maintained by the wave sources and wave detectors, the identical near-distance and far-distance requirements are automatically met.

Figure 2:
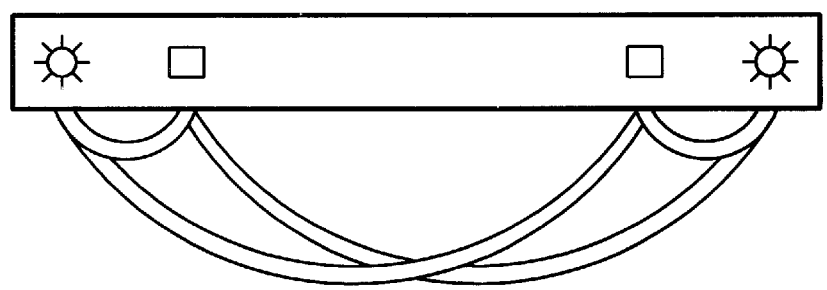
FIG. 2 is a schematic diagram of another sample optical system having two wave sources and two wave detectors having different near-distances and far-distances according to the present invention.

In another exemplary embodiment, multiple wave sources and detectors may be arranged in an asymmetrical configuration that does not satisfy the identical near-distance and far-distance requirements. FIG. 2 is a schematic diagram of another sample optical system with two wave sources and two wave detectors having different near-distances and far-distances according to the present invention. As manifest in the figure, both the near- and far-distances of the source-detector pairs are different. In addition, the banana-shaped paths of the electromagnetic waves (see the figure) reveal that each source-detector pair covers different portions of the target area in different depths. Thus, such source-detector arrangement allows detection of the electromagnetic waves absorbed or scattered through different regions of the target area in different depths.

Figure 3:
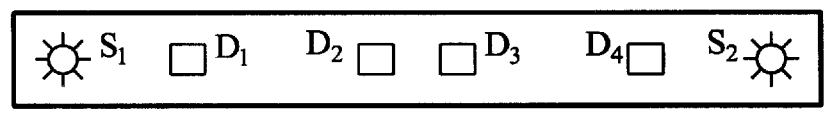
FIG. 3 is a schematic diagram of yet another sample optical system having two wave sources and four wave detectors according to the present invention.

In yet another exemplary embodiment, the foregoing symmetric and asymmetric embodiments can be realized in a single wave source-detector arrangement. FIG. 3 is a schematic diagram of yet another sample optical system having two wave sources and four wave detectors according to the present invention. It is appreciated that not every source-detector pair satisfies the identical near- and far-distance configuration of FIG. 1. For example, although the first and fourth wave detectors ($D_1$ and $D_4$) as well as the second and third wave detectors ($D_2$ and $D_3$) have the identical near- and far-distances from the wave sources ($S_1$ and $S_2$), such near- and far-distances are different for the first and third wave detectors ($D_1$ and $D_3$) or the second and fourth wave detectors ($D_2$ and $D_4$) with respect to the wave sources ($S_1$ and $S_2$). Therefore, by selectively coupling appropriate wave source with wave detector and by irradiating and detecting the electromagnetic waves thereby, either symmetric or asymmetric source-detector arrangement can be attained. Another advantage of such an embodiment is that such a source-detector arrangement allows multiple scanning of a given target area of the medium. For example, the area positioned under the second wave detector ($D_2$) can be scanned by, e.g., six different source-detector pairs such as $S_1$-$D_1$-$D_2$-$S_2$, $S_1$-$D_1$-$D_3$-$S_2$, $S_1$-$D_1$-$D_4$-$S_2$, $S_1$-$D_2$-$D_3$-$S_2$, $S_1$-$D_2$-$D_4$-$S_2$, and $S_1$-$D_3$-$D_4$-$S_2$. Accordingly, the accuracy of the resulting absolute value of the chromophore concentration (and ratios thereof) can be improved.

It is appreciated that the actual configuration of the source-detector assembly does not affect the foregoing methods of determining the absolute values of the chromophore concentrations and ratios thereof. For example, in all of the foregoing equations, the only term that depends on the actual configuration of the source-detector assembly is "L" or "$L_{siDj}$" representing a linear distance between an i-th wave source ($S_i$) and a matching j-th wave detector ($D_j$) which is operatively coupled to the i-th wave source so as to detect the electromagnetic waves irradiated thereby. Because the L value is pre-determined by the design of the source-detector assembly and because other system variables or parameters do not depend upon the L value, the foregoing methods of the present invention can be used regardless of the presence or absence of the symmetry between the wave sources and wave detectors.

The foregoing symmetric source-detector configurations can be applied to construct two-dimensional optical probes for the CWS optical monitoring and imaging systems. In one embodiment, the symmetric wave source-detector arrangement of FIG. 1 can be stacked in an alternating manner to form a four-by-four square or rectangular optical probe, e.g., the first and fourth rows having two wave detectors interposed between two wave sources while the second and third rows having two wave sources interposed between two wave detectors. In another embodiment, such optical probes may be constructed to have different number of wave sources and/or detectors in the horizontal and vertical directions. For example, the arrangement of FIG. 1 can be repeated twice to form a four-by-two probe, six times to form a four-by-six probe, and so on. In yet another embodiment, such symmetric wave source-detector arrangements may also be repeated in an angular fashion to form circular or arcuate optical probes. In addition, the repeated rows (or columns) of the wave sources and wave detectors may be stretched to form trapezoidal optical probes or stacked to form optical probes having parallelogram shapes. Further embodiments of such symmetric source-detector configurations and optical probes having various geometry are provided in the commonly assigned co-pending U.S. non-provisional patent application bearing Ser. No. 09/778,614, entitled "Optical Imaging System with Symmetric Optical Probe" filed on Feb. 6, 2001 which is incorporated herein in its entirety by reference.

It is further appreciated that two-dimensional optical probes for the CWS optical monitoring and imaging systems can also be constructed based on the foregoing asymmetric source-detector configurations. For example, the asymmetric source-detector arrangement can be repeated at any distances and/or in any order or pattern to form square, rectangular, arcuate or circular optical probes. It is noted that such asymmetric wave source-detector arrangement can be repeated (e.g., rows stacked on top of the others) in predetermined distances so that the repeated wave sources and detectors (e.g., a column of wave sources and detectors) satisfy the foregoing near- and far-distance requirements.

The foregoing wave source-detector configurations and optical probes constructed thereby can also be made to be linearly displaced and/or to rotate one or more of the sensors (i.e., wave sources and detectors) while maintaining optical coupling between such sensors and the medium. Such an embodiment enables to scan a specific target area more than once and to provide more measurement data therefrom, e.g., by arranging the wave sources and detectors to scan the target area at multiple speeds, along different scanning paths and/or in different scanning angles, and the like. Regardless of actual configurations of the source-detector arrangement, such optical probes with mobile sensor elements enable measurement of the absolute values of the chromophores and/or construction of images thereof by using fewer wave sources and detectors. Further details regarding such optical probes with mobile sensors and techniques of directly obtaining images therefrom are provided in the commonly assigned co-pending U.S. non-provisional patent application bearing Ser. No.09/778,617, entitled "Optical Imaging System for Direct Image Construction" filed on Feb. 6, 2001 which is incorporated herein in its entirety by reference.

In operation, a source module with at least one wave source and a detector module having at least one wave detector are provided to a scanning surface of an optical probe which is operatively connected to a main body of an optical system. Alternatively, the wave source and/or detector modules may be disposed in the main body and optical fibers may be provided to connect the source and detector modules to openings provided on the scanning surface of the optical probe. Any conventional wave sources and detectors may be used for such optical prove. It is preferred, however, that the wave sources irradiate electromagnetic waves in the near-infrared range between 500 nm and 1,200 nm or, in particular, between 600 nm and 900 mn and that the wave detectors have appropriate sensitivity to the foregoing electromagnetic waves. The optical probe is placed on a target area of the physiological medium, with its scanning surface disposed on the target area to form an optical coupling therebetween. The source module is activated so that at least two sets of electromagnetic waves having different wave characteristics are irradiated into the medium. The detector module then picks up different sets of electromagnetic waves irradiated by the wave source, propagated through the medium, and directed toward the wave detector. The wave detector generates electric signals which are delivered to the processing module of the main body of the optical system. Based on the experimentally measured intensities of the electromagnetic waves and at least one system parameter such as extinction or scattering coefficients of the chromophores, the processing module computes the absolute values of the concentration of oxygenated and deoxygenated hemoglobins or the oxygen saturation.

It is noted that the optical system according to the present invention may include an equation solving module which is operationally separate from the processing module. Such an equation solving module may include variety of numerical models designed perform one or more of the foregoing methods of the present invention.

Although the foregoing disclosure has been directed toward obtaining the absolute values of the concentrations of oxygenated and deoxygenated hemoglobins (and/or their ratios), the foregoing optical systems and methods may be applicable to obtain the absolute values of other substances in the medium or properties thereof. For example, the systems and methods of the present invention may be directly applied or modified to determine the absolute values of the concentrations (or their ratios) of other chromophores such as lipids, cytochromes, water, and the like. Depending upon the absorption or scattering coefficients, the wavelengths of the electromagnetic waves may be adjusted for better resolution. In addition, chemical compositions may be added to the medium to enhance optical interaction or interference of chromophores in the medium or to convert an non-chromatic substance of the medium into a chromophore.

As described hereinabove, the foregoing optical systems and methods of the present invention are preferred to be incorporated to the continuous wave spectroscopic technology. However, such systems and methods may readily be incorporated into the time-resolved and phase-modulation spectroscopic technologies as well.

The optical systems and methods according to the present invention find a variety of medical applications. As described above, such optical monitoring and/or imaging systems and methods may be applied to measure the absolute values of concentrations of oxygenated and deoxygenated hemoglobin and/or their ratio. Such optical systems will be beneficial in non-invasively diagnosis of ischemic conditions and/or ischemia in various organs and tissues such as, e.g., a brain (stroke), heart (ischemia) or other physiological abnormalities originating from or characterized by abnormally low concentration of oxy-hemoglobin. In addition, presence of cancerous tumors in various internal organs, breasts, and skins may be easily detected as well. Such optical systems and methods may further be applied to cells disposed in epidermis, corium, and organs such as a lung, liver, and kidney. Such optical systems and methods may also be applied to diagnose vascular occlusion during or after surgical procedures including transplantation of tissues, skins, and organs, e.g., heart, lung, liver, and kidney.

Following examples describe simulation and experimental results obtained by the optical systems and methods thereof according to the present invention. All simulation and experimental results indicate that the optical systems and methods thereof provide accurate predictions and/or measurements of the concentrations of the hemoglobins and the oxygen saturation.

EXAMPLE 1

The diffusion equation (3b) was numerically solved for optical proves with multiple wave sources and detectors arranged in various configurations. The equations were applied to a sample physiological medium such as a semi-infinite, homogeneous diffuse medium with different background optical properties. Diffuse reflectances were calculated according to an imaging source approach disclosed in an article entitled, "Boundary conditions for the diffusion equation in radiative transfer" by R. C. Haskell et al. and published in Journal of Optical Society of America, vol. 11, p. 2727–2741, 1994. Values of G (i.e., the ratio of $F^{\lambda_1}$ to $F^{\lambda_2}$ simulated at different wavelengths) were estimated at different levels of oxygen saturation ($SO_2$) and fitted as a polynomial thereof.

Figure 4A:
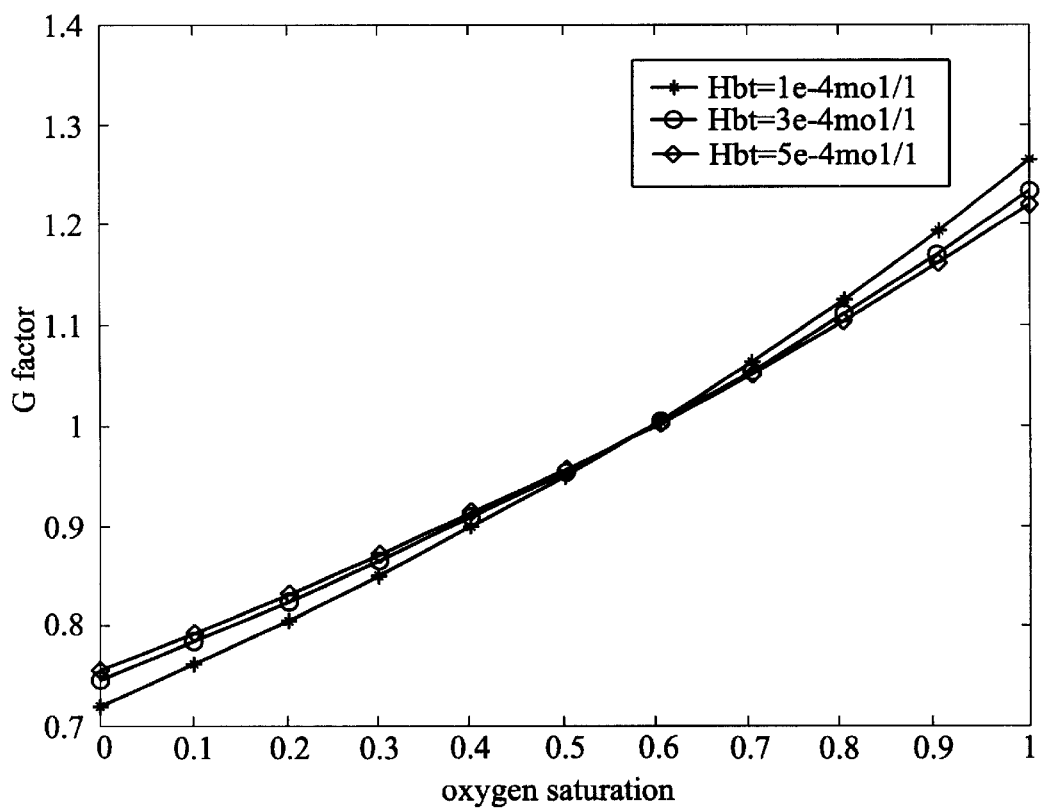
FIG. 4A is a plot of simulated values of G (i.e., a ratio of $F_1$ to $F_2$) at different wavelengths as a function of oxygen saturation according to the present invention.
Figure 4B:
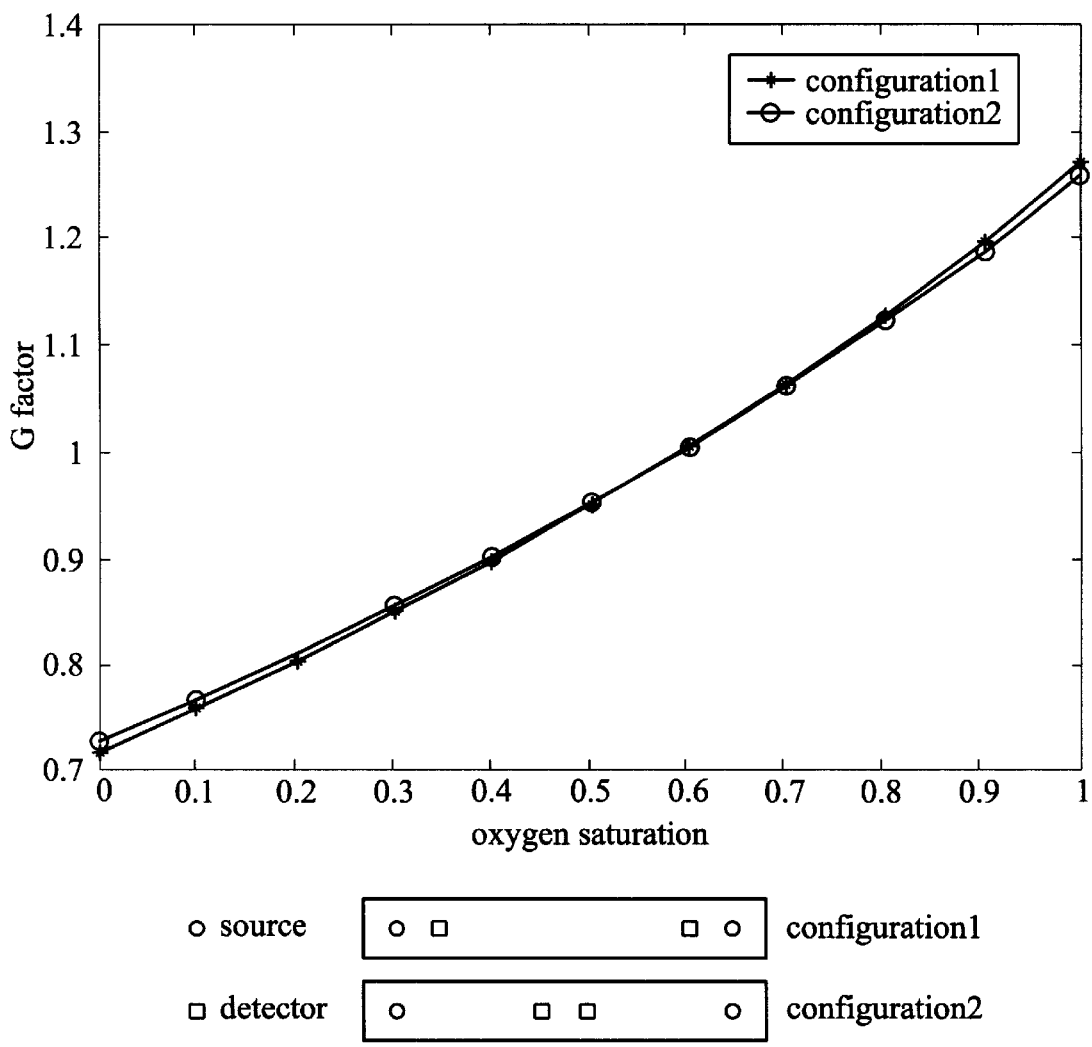
FIG. 4B is another plot of simulated values of G at different wavelengths as a function of oxygen saturation according to the present invention.
Figure 4C:
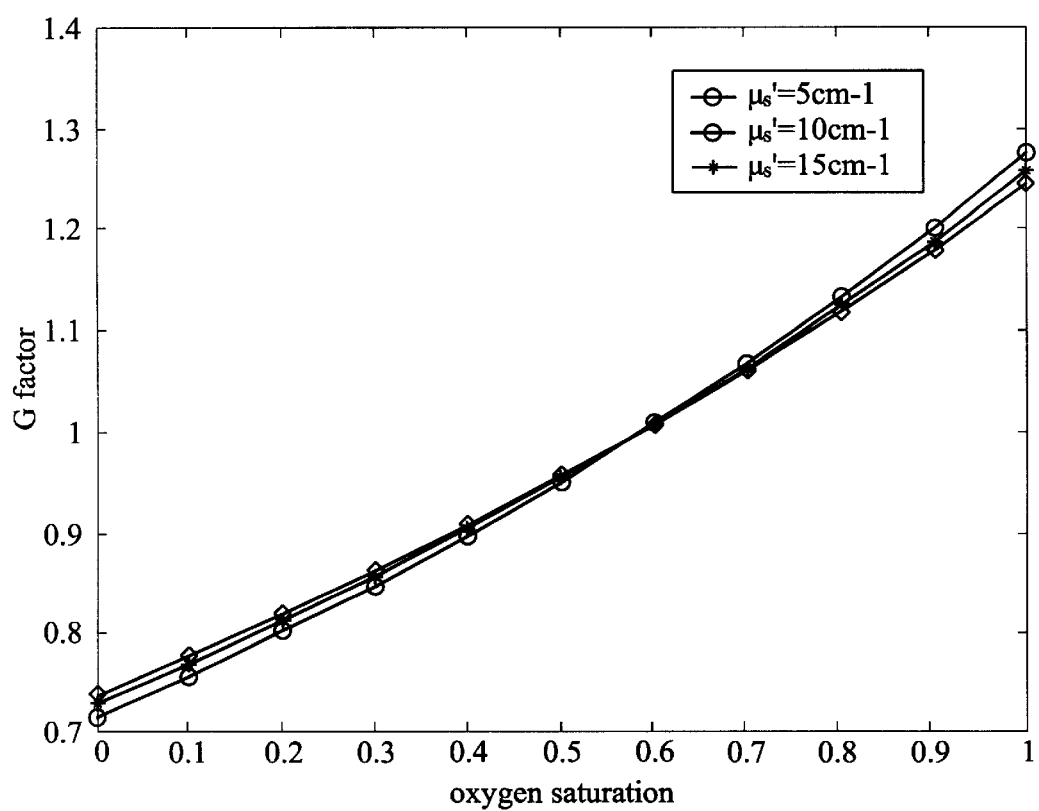
FIG. 4C is yet another plot of simulated values of G at different wavelengths as a function of oxygen saturation according to the present invention.

FIGS. 4A to 4C are plots of G's as a function of oxygen saturation ($SO_2$). As shown in the figures, all simulation results revealed distinct one-to-one correlations between G and oxygen saturation ($SO_2$). In addition, all of the figures indicated that dependence of G upon oxygen saturation was substantially insensitive to simulated source-detector configurations and background optical properties.

Conventional curve-fitting methods, e.g., the least-squares method, were applied to numerically estimate the coefficients of polynomial equation (10) (i.e., $\alpha_0, \alpha_1, \alpha_2, \alpha_3 \ldots$). For example, in a system with background reduced scattering coefficient of 10 $cm^{-1}$ and total hemoglobin concentration of $10^{-4}$ mol/liter irradiated by the electromagnetic waves having wavelengths of 780 nm and 830 nm, following polynomial equation was obtained and found to satisfactorily approximated the relation between G and oxygen saturation ($SO_2$):

$$G = \frac{F^{\lambda_1}}{F^{\lambda_2}} = 0.728 + 0.399 \cdot SO_2 + 0.064 \cdot SO_2^2 + 0.067 \cdot SO_2^3 \quad (18)$$

EXAMPLE 2

Figure 5:
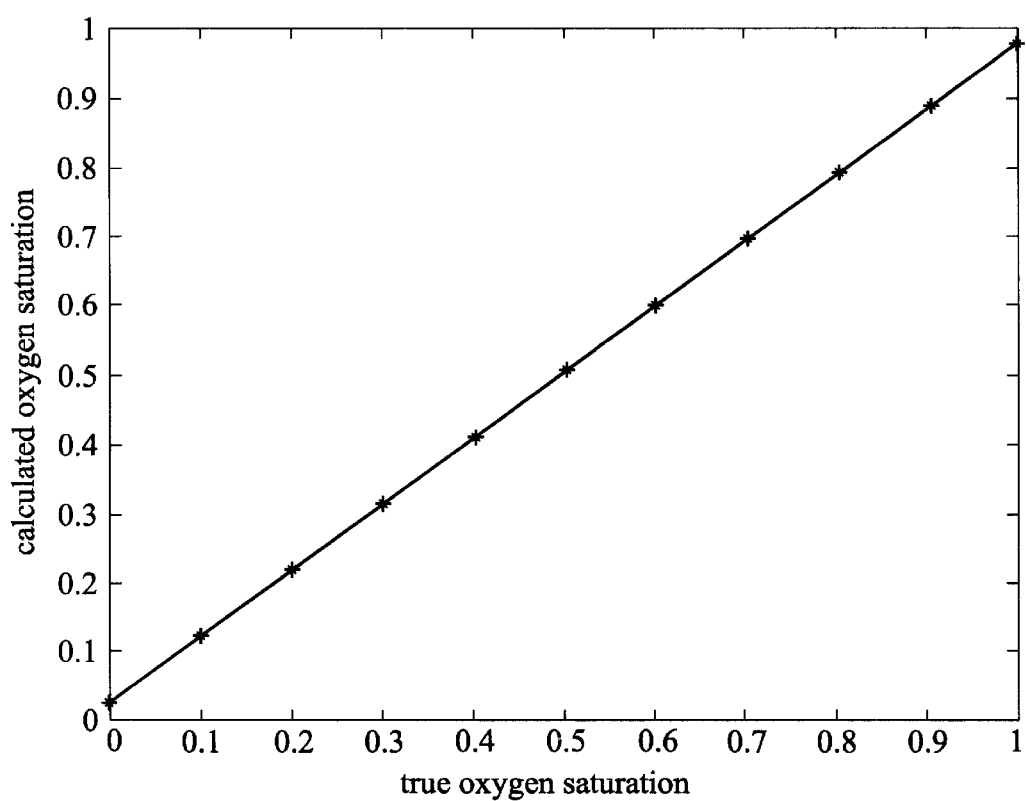
FIG. 5 is another plot of calculated oxygen concentration versus true oxygen saturation in a medium with a different background scattering coefficient and total hemoglobin concentration according to the present invention.

Further simulations were performed in a system with the background scattering of 7 $cm^{-1}$ and the total hemoglobin concentration of $2 \times 10^{-4}$ mol/liter. In the simulations, oxygen saturation ($SO_2$) was varied from 0 to 100%. FIG. 5 is a plot of calculated oxygen saturation contrasted against true oxygen saturation. Although the background properties used to find the correlation between G and oxygen saturation were quite different, the estimated oxygen concentration was accurate with a systematic error of about a few percent.

EXAMPLE 3

An exemplary optical system was prepared and hemoglobin concentrations and the oxygen saturation were monitored before and after occlusion of arteries of an extremity in a human subject. In this Example was used the optical system of FIG. 1 including two wave sources and two wave detectors arranged in a linear fashion. Two wave detectors were linearly disposed and separated by 6 mm. Two wave sources were disposed outside of each wave detector so that the left wave source was disposed at the left side of the left wave detector at a distance of 9 mm, and the right wave source disposed at the right side of the right wave detector at a distance of 9 mm. Accordingly, each pair of the wave sources and detectors had identical near-distances and far-distances.

The wave sources had an outer diameter of 2 mm and included laser diodes (model HL6738MG and HL8325G, both available from Thorlabs, Inc., Newton, N.J.) for irradiating electromagnetic waves with wavelengths 690 nm and 830 nm, respectively. Photo-detectors (model OPT202, available from Barr-Brown, Tucson, Ariz.) were used as the wave detectors.

A cuff was placed around the upper arm and the optical probe was disposed at the fore arm. After the subject was stabilized, cuff pressure was increased to about 160 mmHg in about 35 seconds, held at the same level for about 40 seconds, and then released to the atmospheric level. Absolute concentrations of total hemoglobin, oxygenated hemoglobin, and deoxygenated hemoglobin were monitored, and the oxygen saturation was calculated therefrom.

Figure 7:
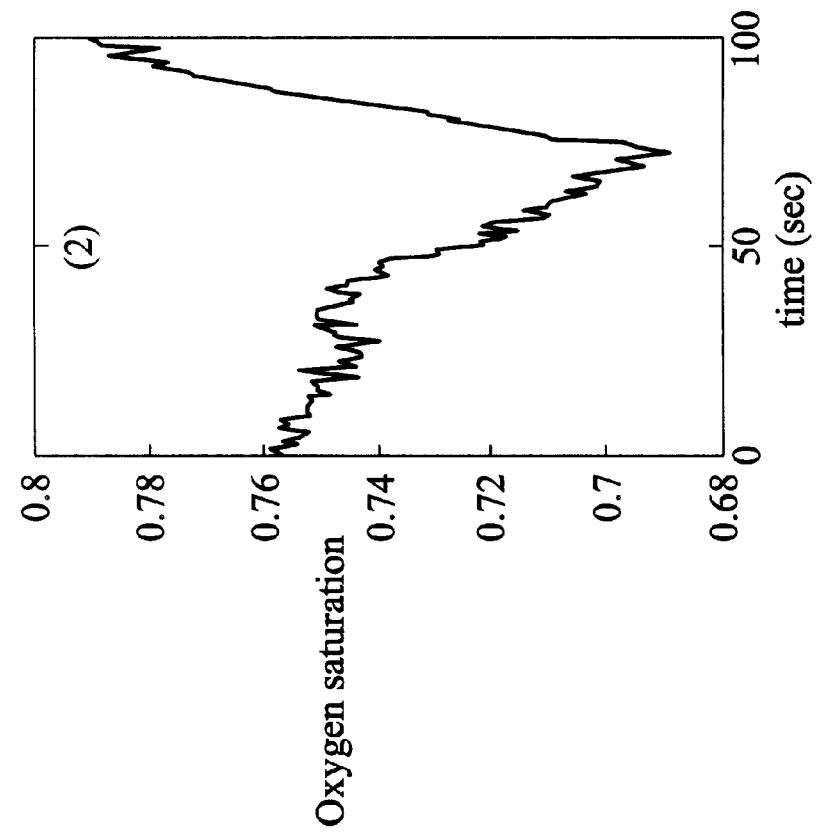
FIG. 7 is a time-course plot of oxygen saturation according to the present invention.
Figure 6:
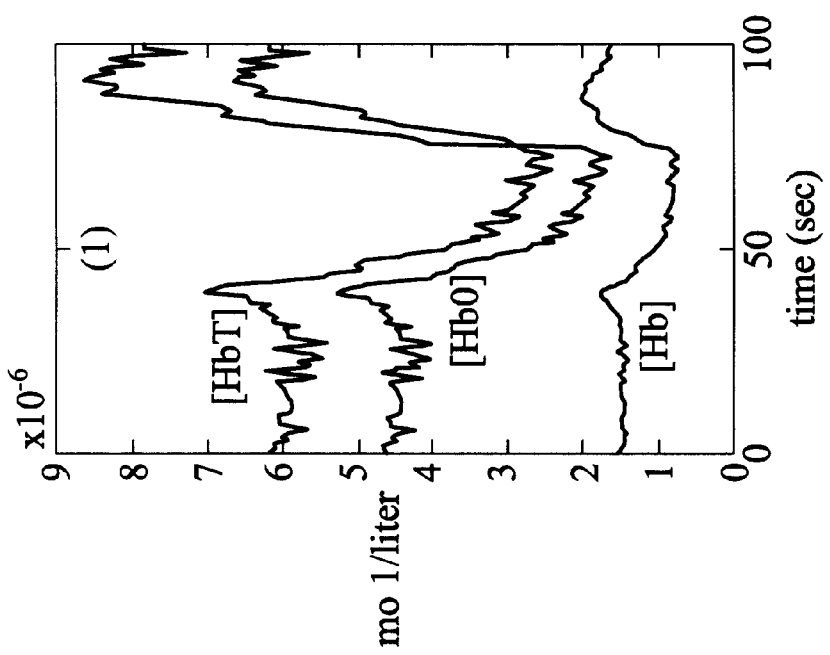
FIG. 6 is a time-course plot of total hemoglobin (HbT) concentration, oxygenated hemoglobin (HbO) concentration, and deoxygenated hemoglobin (Hb) concentration according to the present invention.

FIG. 6 is a time-course plot of total hemoglobin (HbT) concentration, oxygenated hemoglobin (HbO) concentration, and deoxygenated hemoglobin (Hb) concentration according to the present invention, and FIG. 7 is a time-course plot of oxygen saturation according to the present invention. As shown in the figures, hemoglobin concentrations and oxygen saturation decreased sharply during the initial phase of occlusion, followed by a gradual decrease thereof. After the release, concentrations and oxygen saturation showed rapid increase. These results demonstrated that the optical systems and methods according to the present invention provided accurate predictions of the hemoglobin concentrations as well as the oxygen saturation. These results also showed that the optical systems possessed proper temporal response characteristics.

EXAMPLE 4

Figure 8:
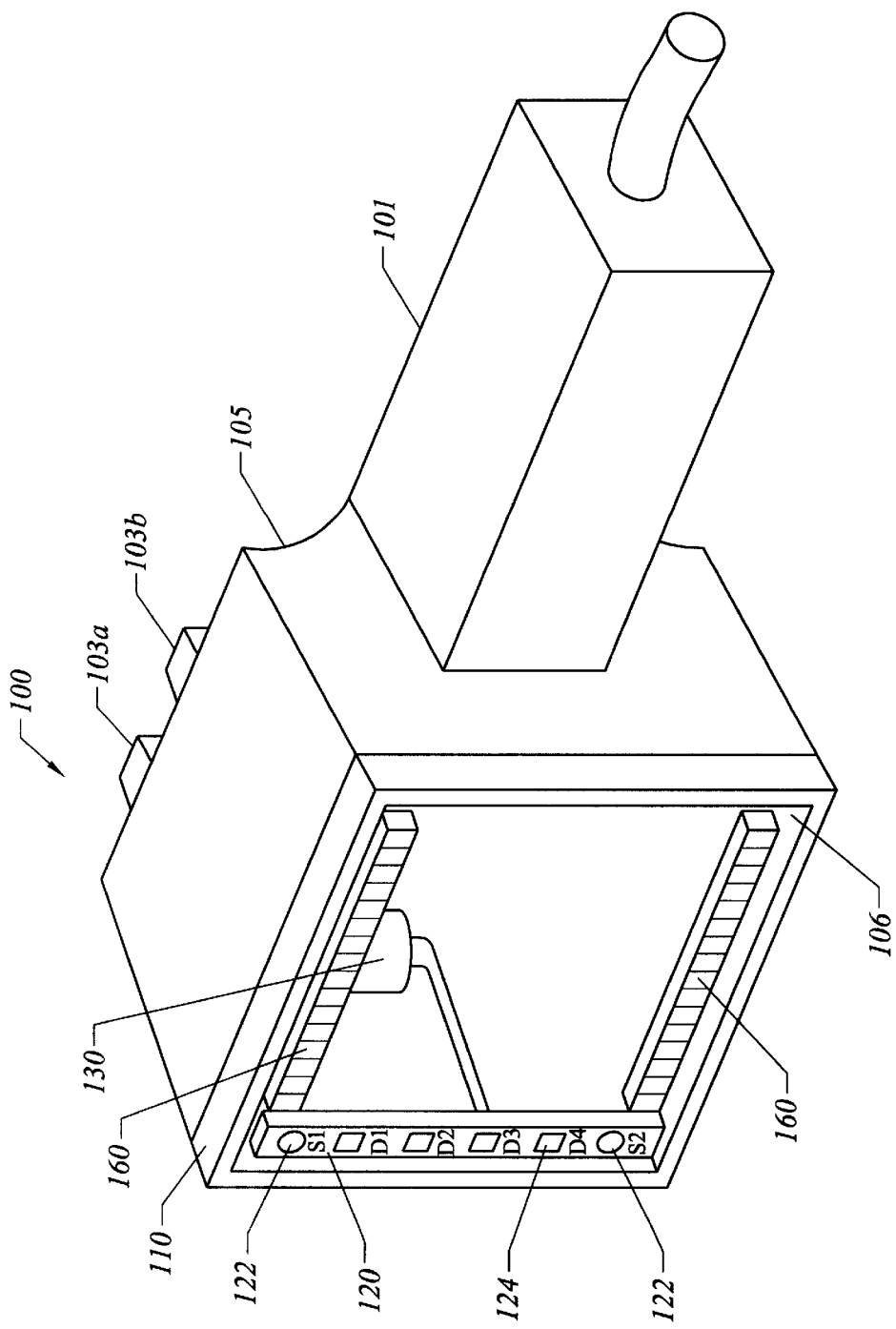
FIG. 8 is a schematic diagram of an optical imaging system according to the present invention.

An exemplary optical imaging system was constructed to obtain images of two-dimensional distribution of blood volume and oxygen saturation in female human breasts. FIG. 8 is a schematic diagram of a prototype optical imaging system according to the present invention.

Prototype optical imaging system 100 included a handle 101 and a main housing 105. Handle 101 was made of poly-vinylchloride (PVC) and acrylic stock, and provided with two control switches 103a, 103b for controlling operations of various components of system 100. Main housing 105 included a body 110, a movable member 120, an actuator member 130, an imaging member (not shown), and a pair of guiding tracks 160.

Body 110 was shaped as a substantially square block (3.075"×2.8"×2.63") and provided with barriers along its sides. Body 110 was arranged to movably couple with rectangular movable member 120 (1.5"×2.8"×1.05") designed to linearly translate along a path substantially parallel with one side of body 110.

Movable member 120 was arranged to have the source-detector arrangement which was similar to that of FIG. 3. For example, movable member 120 included two wave sources 122, $S_1$ and $S_2$, each of which was capable of irradiating electromagnetic waves having different wavelengths. In particular, each wave source 122 included two laser diodes, HL8325G and HL6738MG (ThorLabs, Inc., Newton, N.J.), where each laser diode irradiated the electromagnetic waves with wavelengths of 690 nm and 830 nm, respectively. Movable member 120 also included four identical wave detectors 124 such as photo-diodes $D_1$, $D_2$, $D_3$, and $D_4$, (OPT202, Burr-Brown, Tucson, Ariz.) which were interposed substantially linearly between wave sources 122. Wave sources 122 and detectors 124 were spaced at identical distances such that the foregoing sensors 122, 124 satisfy the foregoing near- and far-distance requirements or symmetry requirements.

Actuator member 130 included a high-resolution linear-actuating-type stepper motor (Model 26000, Haydon Switch and Instrument, Inc., Waterbury, Conn.) and a motor controller (Spectrum PN 42103, Haydon Switch and Instrument, Inc.). Actuator member 130 was mounted on body 110 and engaged with movable member 120 so as to linearly translate movable member 120 along guiding tracks 160 fixedly positioned along the linear path. A pair of precision guides (Model 6725K11, McMaster-Carr Supply, Santa Fe Springs, Calif.) was used as guiding tracks 160.

The imaging member was provided inside handle 101 and had a data acquisition card (DAQCARD 1200, National Instruments, Austin, Tex.). Main housing 105 was made of acrylic stocks and constructed to open at its front face. Perspex Non-Glare Acrylic Sheet (Liard Plastics, Santa Clara, Calif.) was installed on a front face 106 of housing 105 and used as a protective screen to protect wave sources 122 and detectors 124 from damages.

In operation, movable member 120 was positioned in its starting position, i.e., the far-left side of body 105. An operator turned on the main power of system 100 and tuned wave sources 122 and detectors 124 by running scanning system software. A breast of a human subject was prepped and body 105 was positioned on the breast so that sensors 122, 124 of movable member 120 were placed in a first target area of the breast and formed appropriate optical coupling therewith. The first target area was scanned by clicking one control switch 103a on handle 101. Actuator member 130 translated movable member 120 linearly along one side of body 110 along guide tracks 160.

Wave sources 122 were synchronized to ignite their laser diodes in a pre-selected sequence. For example, a first laser diode of the wave source, $S_1$, was arranged to irradiate electromagnetic waves of wavelength 690 nm and wave detectors 124 detected the waves and generated a first set of output signals in response thereto. During the foregoing irradiation and detection period which generally lasted about 1 msec (with duty cycle from 1:10 to 1:1,000), all other laser diodes were turned off to minimize interference noises. After completing the irradiation and detection, the first laser diode of the wave source, $S_1$, was turned off and the first laser diode of the wave source, $S_2$, was turned on to irradiate electromagnetic waves of the same wavelength, 690 nm. Wave detectors 124 detected the waves and generated a second set of output signals accordingly. Other laser diodes were maintained at off positions during the foregoing irradiation and detection period as well. Similar procedures were repeated to the second laser diodes of the wave sources, $S_1$ and $S_2$, where both second laser diodes were arranged to sequentially irradiate the electromagnetic waves having wavelengths 830 nm.

The imaging member was also synchronized with wave sources 122 and detectors 124 and sampled the foregoing sets of output signals in a pre-selected sampling rate. In particular, the imaging member was arranged to process such output signals by defining a first and second scanning units, where the first scanning unit was comprised of the wave sources, $S_1$ and $S_2$, and the wave detectors, $D_1$ and $D_4$, and the second scanning unit was made up of the wave sources, $S_1$ and $S_2$, and the wave detectors, $D_2$ and $D_3$. Both of the first and second scanning units had the source-detector arrangement that satisfied the foregoing symmetry requirements. Therefore, absolute values of the concentrations of the oxygenated and deoxygenated hemoglobins were obtained by the equations (8a) and (8b), and oxygen saturation, $SO_2$, by equation (9b). Furthermore, relative values of blood volume (i.e., temporal changes thereof) was calculated by assessing the changes in hematocrit in the target areas.

Actuator member 130 was also synchronized with the foregoing irradiation and detection procedures so that wave sources 122 and detectors 124 scanned the entire target area (i.e., irradiating electromagnetic waves thereinto, detecting such therefrom, and generating the output signals) before they were moved to the next adjacent region of the target area by actuator member 130. When movable member 120 reached the opposing end of body 110, actuator member 130 translated movable member 120 linearly to its starting position. The foregoing irradiation and detection procedures were repeated during such backward linear movement of movable member 120 as well. After the scanning procedure was completed, the operator pushed the other control switch 103b to send a signal to the imaging member which started image construction process and provided two-dimensional images of spatial distribution of the oxygen saturation in the target area and the temporal changes in the blood volume therein.

Figure 9A:
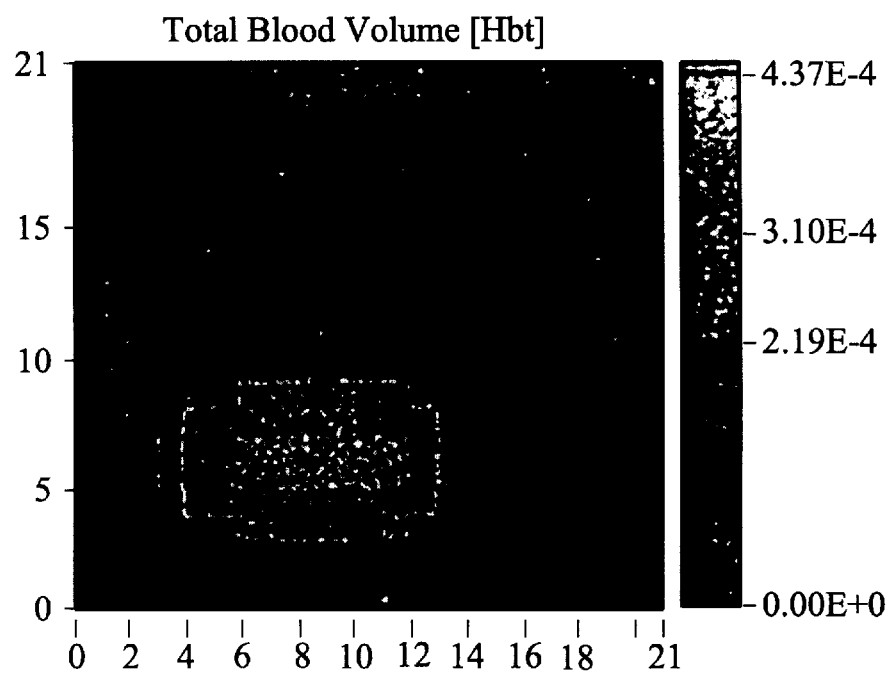
FIGS. 9A and 9B are images of blood volume of normal and abnormal breast tissues, respectively, both of which are measured by the optical imaging system of FIG. 8 according to the present invention.
Figure 9B:
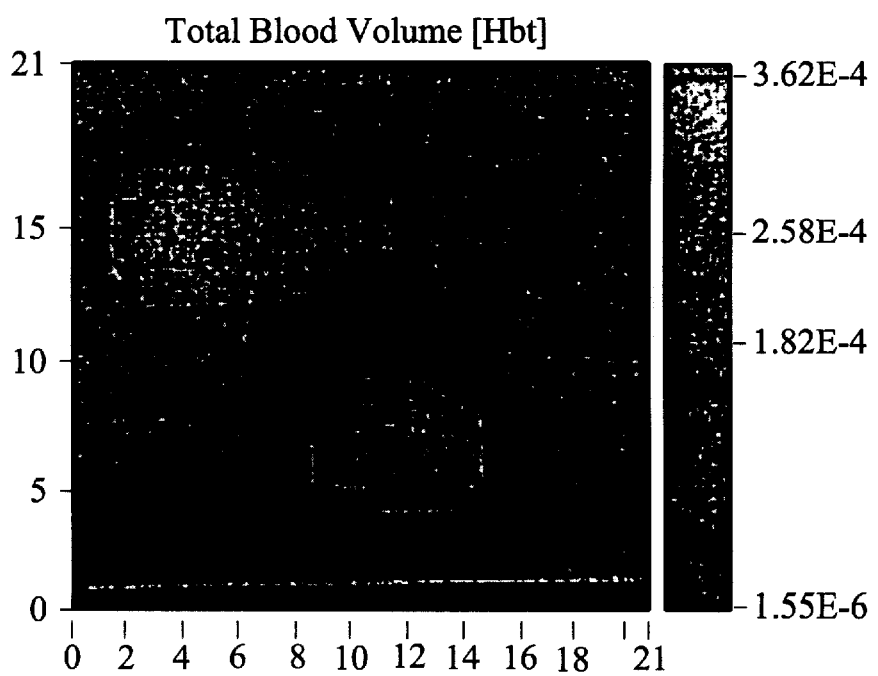
Figure 10A:
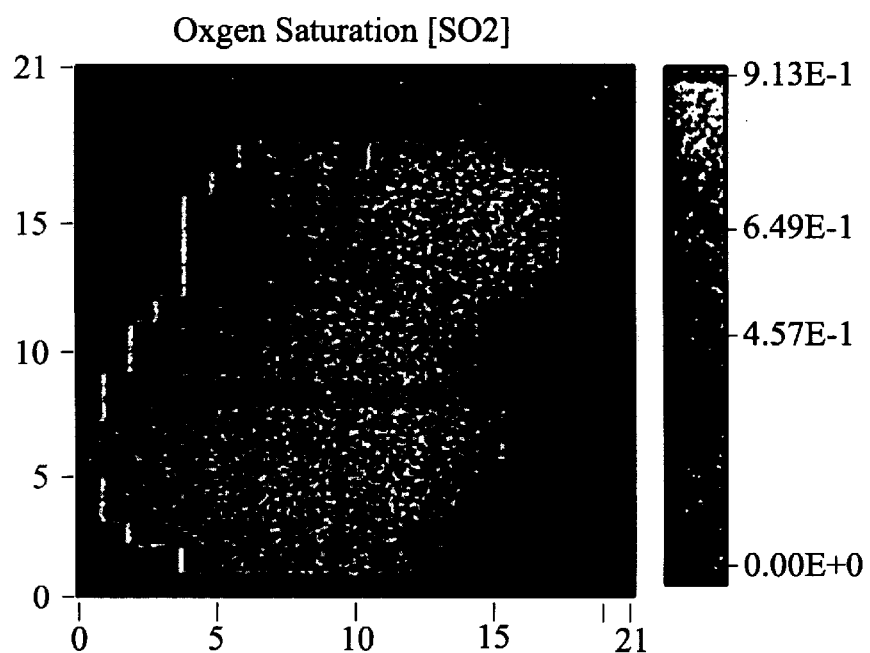
FIGS. 10A and 10B are images of oxygen saturation of normal and abnormal breast tissues, respectively, both of which are measured by the optical imaging system of FIG. 8 according to the present invention.
Figure 10B:
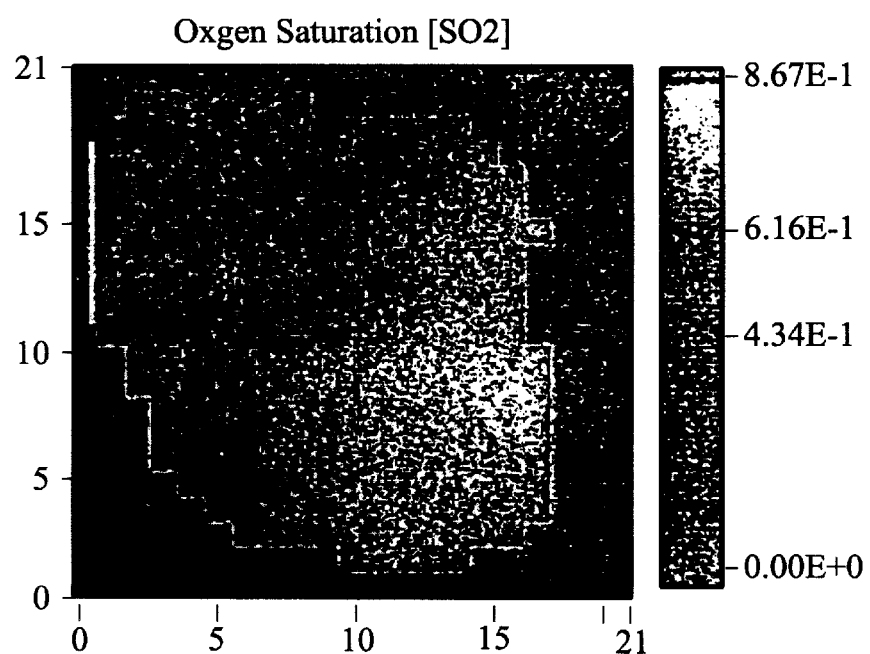

FIGS. 9A and 9B are two-dimensional images of blood volume in normal and abnormal breast tissues, respectively, both measured by the optical imaging system of FIG. 8. In addition, FIGS. 10A and 10B are two-dimensional images of oxygen saturation in normal and abnormal breast tissues, respectively, both measured by the optical imaging system of FIG. 8 according to the present invention. As shown in the figures, the optical imaging system provided that normal tissues had the higher oxygen saturation (e.g., over 70%) in the area with the maximum blood volume. However, the higher oxygen saturation in the corresponding area of the abnormal tissues was as low as 60%.

It is to be understood that, while various embodiments of the invention has been described in conjunction with the detailed description thereof, the foregoing is intended only to illustrate and not to limit the scope of the invention, which is defined by the scope of the appended claims. Other embodiments, aspects, advantages, and modifications are within the scope of the following claims.

What is claimed is:

1. A system for determining concentrations of chromophores in a physiological medium, comprising:

first and second wave sources to irradiate into said medium at least two sets of electromagnetic radiation having different wave characteristics;

first and second wave detectors to detect electromagnetic radiation transmitted through said medium, wherein a distance between said first wave source and said first wave detector is different than a distance between said second wave source and said second wave detector; and a processing module operatively coupled with said first and second wave detectors to determine an absolute value of a concentration of a chromophore in said medium from continuous wave electromagnetic radiation irradiated from said first and second wave sources and detected by said first and second wave detectors.

2. A system according to claim 1, wherein said chromophores are hemoglobins including oxygenated hemoglobin and deoxygenated hemoglobin.

3. A system according to claim 1, wherein said physiological medium includes cells of at least one of organs, tissues, and body fluids.

4. A system according to claim 3, wherein at least some cells are abnormal.

5. A system according to claim 4, wherein said abnormal cells are tumor cells.

6. A system according to claim 4, wherein said cells are disposed in at least one of epidermis, and corium of an internal organ including at least one of a brain, heart, lung, liver, and kidney.

7. A system according to claim 4, wherein said cells are those of a transplanted organ.

8. A system according to claim 7, wherein said transplanted organ includes at least one of a brain, heart, lung, liver, and kidney.

9. A system according to claim 1, wherein said wave characteristics include at least one of wavelengths, phase angles, amplitudes and harmonics.

10. A system according to claim 9, wherein a first set of said electromagnetic waves has a first wavelength and a second set of said electromagnetic waves has a second wavelength, which is different from said first wavelength.

11. A system according to claim 9, wherein a first set of said electromagnetic waves includes a first carrier wave and a second set of said electromagnetic waves includes a second carrier wave which has wave characteristics different from those of said first carrier wave.

12. A system according to claim 11, wherein said wave characteristics include at least one of wavelengths, phase angles, amplitudes, harmonics, and a combination thereof.

13. A system according to claim 1, wherein said processing module determines said absolute value utilizing a parameter accounting for optical interaction properties of electromagnetic waves with said medium.

14. A system according to claim 13, wherein said processing module uses a mathematical expression including at least one parameter dependent on one of: optical properties of said medium and configuration of said source module and detector module.

15. A system according to claim 14, wherein said mathematical expression comprises a polynomial of at least one of said concentrations and said ratios thereof.

16. A system according to claim 13, wherein said mathematical expression includes a term substantially dependent on one or more of: optical properties of said medium and configuration of said first and second wave sources and first and second wave detectors, which term is approximated as a constant.

17. A system according to claim 1, wherein said processing module uses the mathematical expression:

$$I = \alpha\beta\gamma I_o \exp\{-BL\delta\Sigma_i(\epsilon_i C_i)+\sigma\},$$

wherein $I_o$ is a variable for an intensity of electromagnetic waves irradiated by a wave source, I is a variable for an intensity of electromagnetic waves detected by a wave detector, $\alpha$ is a parameter associated with at least one of said wave source and medium, $\beta$ is a parameter associated with at least one of said wave detector and medium, $\gamma$ is one of a proportionality constant and a parameter associated with at least one of said wave source, wave detector, and medium, B is a parameter accounting for a length of an optical path of electromagnetic waves through said medium and associated with at least one of said wave source, wave detector, and medium, L is a parameter accounting for a distance between said wave source and said wave detector, $\delta$ is one of a proportionality constant and a parameter associated with at least one of said wave source, wave detector, and medium, $\epsilon_i$ is a parameter accounting for an optical interaction between electromagnetic waves and an i-th chromophore in said medium, $C_i$ is a variable denoting concentration of said i-th chromophore, and $\sigma$ is one of a proportionality constant and a parameter associated with at least one of said wave source, wave detector, and medium.

18. A system according to claim 17, wherein said parameter B is a path length factor.

19. A system according to claim 17, wherein said parameter $\epsilon_i$ is at least one of a medium extinction coefficient, medium absorption coefficient, and medium scattering coefficient.

20. A system according to claim 1, wherein said processing module uses the mathematical expression:

$$I_{mn} = \alpha_m \beta_n \gamma I_{o,m} \exp\{-B_{mn}L_{mn}\delta\Sigma_i(\epsilon_i C_i)+\sigma\},$$

wherein $I_{o,m}$ is a variable for an intensity of electromagnetic waves irradiated by an m-th wave source, $I_{mn}$ is a variable for an intensity of electromagnetic waves irradiated by said m-th wave source and detected by an n-th wave detector, $\alpha_m$ is a parameter associated with at least one of said m-th wave source and medium, $\beta_n$ is a parameter associated with at least one of said n-th wave detector and medium, $\gamma$ is one of a proportionality constant and a parameter associated with at least one of said m-th wave source, n-th wave detector, and medium, $B_{mn}$ is a parameter accounting for a length of an optical path of electromagnetic waves through said medium and associated with at least one of said m-th wave source, n-th wave detector, and medium, $L_{mn}$ is a parameter accounting for a distance between said m-th wave source and n-th wave detector, $\delta$ is one of a proportionality constant and a parameter associated with at least one of said m-th wave source, n-th wave detector, and medium, $\epsilon$ is a parameter accounting for an optical interaction between electromagnetic waves and an i-th chromophore included in said medium, $C_i$ is a variable denoting concentration of said i-th chromophore, and $\sigma$ is one of a proportionality constant and a parameter associated with at least one of said m-th wave source, n-th wave detector, and medium, wherein both of said subscripts m and n are non-zero positive integers.

21. A system according to claim 20, wherein said parameter $B_{mn}$ is a path length factor associated with at least one of said m-th wave source, n-th wave detector, and medium.

22. A system according to claim 20, wherein said parameters $\gamma$ and $\delta$ are configured to be substantially close to a unity so that said expression is simplified to $$I_{mn} = \alpha_m \beta_n I_{o,m} \exp\{-B_{mn}L_{mn}\Sigma_i(\epsilon_i C_i)+\sigma\}.$$

23. A system according to claim 1, wherein said first and second wave detectors are disposed substantially along a straight line, and said first and second wave sources are disposed on opposite sides of the straight line.

24. A system according to claim 1, further comprising a third wave detector and said first, second and third wave detectors disposed substantially along a straight line.

25. A system for determining concentrations of chromophores in a physiological medium, comprising:
one or more sources irradiating into said medium at least two sets of near-infrared electromagnetic waves having different wave characteristics;
one or more detectors detecting electromagnetic waves transmitted through said medium;
input means for entering input parameter data; and
a processing module determining absolute values of at least one of said concentrations,
wherein said determination is not based on measuring phase characteristics of the electromagnetic radiation received from said one or more detectors, or the response of the medium to an electromagnetic impulse from said one or more sources.

26. A system for determining concentrations of chromophores in a physiological medium, comprising:
   at least one source for irradiating into said medium at least two sets of electromagnetic waves having different wave characteristics;
   at least one detector for detecting electromagnetic waves transmitted through said medium;
   a processor coupled to the at least one detector computing one of: absolute values of said concentrations and ratios of said concentrations,
   wherein said computation is based only on intensity measurements of continuous wave electromagnetic radiation from the source module.

27. A method for determining concentrations of chromophores in a physiological medium using a system having at least one wave source and at least one wave detector, wherein electromagnetic waves are irradiated by said wave source, transmitted through the physiological medium, and detected by said wave detector, the method comprising the steps of:
   irradiating at least two sets of electromagnetic waves having different wave characteristics to obtain a plurality of measurements;
   providing a mathematical expression relating said plurality of measurements to parameters of the system, and parameters associated with said medium;
   eliminating source-dependent and detector-dependent parameters from the provided mathematical expression; and
   determining an absolute value of at least one of said concentrations, wherein said determination is based only on intensity measurements of continuous wave electromagnetic radiation and pre-determined chromophore-dependent parameters.

28. The method of claim 27, wherein the mathematical expression includes a wave equation is expressed as:

$$I=\alpha\beta\gamma I_o \exp\{-BL\delta\Sigma_i(\epsilon_i C_i)+\sigma\},$$

wherein $I_o$ is a variable for an intensity of electromagnetic waves irradiated by at least one source, I is a variable for an intensity of electromagnetic waves detected by at least one detector, $\alpha$ is a parameter associated with at the least one source and the medium, $\beta$ is a parameter associated with the at least one detector and the medium, $\gamma$ is one of a proportionality constant and a parameter associated with at least one source, detector and medium, B is a parameter accounting for lengths of optical paths of electromagnetic waves through said medium and associated with at least one source, detector and medium, L is a parameter accounting for a distance between the source and the detector, $\delta$ is one of a proportionality constant and a parameter associated with at least one of the source, detector, and medium, $\epsilon_i$ is a parameter accounting for A interaction between electromagnetic waves and an i-th chromophore in said medium, $C_i$ is a variable denoting concentration of said i-th chromophore, and $\sigma$ is one of a proportionality constant and a parameter associated with at least one of said source, detector, and medium.

29. A method for determining concentrations of chromophores in a physiological medium using a system having at least one wave source and at least one wave detector by application of a wave equation having a form:

$$I_{mn}=\alpha_m\beta_n\gamma I_{o,m} \exp\{-B_{mn}L_{mn}\delta\Sigma_i(\epsilon_i C_i)+\sigma\},$$

wherein $I_{o,m}$ is a variable representing an intensity of electromagnetic waves irradiated by the m-th wave source, $I_{mn}$ is a variable for an intensity of electromagnetic waves irradiated by the
   m-th wave source and detected by the n-th detector, $\alpha_m$ is a parameter associated with the m-th wave source and the medium, $\beta_n$ is a parameter associated with the n-th wave detector and the medium, $\gamma$ is one of a proportionality parameter associated with at least one of wave source, detector, and medium, $B_{mn}$ is a parameter accounting for lengths of optical paths of electromagnetic waves through said medium and associated with the m-th wave source, n-th wave detector, and the medium, $L_{mn}$ is a parameter accounting for a distance between the m-th wave source and the n-th wave detector, $\delta$ is one of a proportionality parameter associated with at least one wave source, wave detector, and medium, $\epsilon_i$ is a parameter accounting for an optical interaction between electromagnetic waves and an i-th chromophore in said medium, $C_i$ is a variable for concentration of said i-th chromophore, and $\sigma$ is one of a proportionality parameter associated with a wave source, wave detector, and medium, said method comprising the steps of:
   irradiating a first and second set of electromagnetic waves having different wave characteristics and measuring signals received from the medium to obtain two sets of equations relating the measured signals with unknown parameters in the wave equation;
   eliminating at least one of the parameters $\alpha_m$, $\beta_n$, $\gamma$, $\delta$, and $\sigma$ from the wave equation using the first and second set of equations to obtain a third set of equations;
   obtaining an expression for an absolute value of at least one of said concentrations based on values associated with $I_{mn}$, $I_{o,m}$, and $\epsilon_i$, following the step of eliminating.

30. The method of claim 29 further comprising the steps of:
   applying said system to said physiological medium including cells of at least one of organs, tissues, and body fluids; and
   measuring said absolute value of at least one of said concentrations based on said values of $I_{mn}$, $I_{o,m}$, and $\epsilon_i$.

31. The method of claim 30, wherein said measuring step comprises the step of:
   monitoring at least one of oxygenated hemoglobin concentration, deoxygenated hemoglobin concentration, and a ratio thereof.

32. The method of claim 31 further comprising the step of determining a presence of tumor cells over a finite area of said medium.

33. The method of claim 31 further comprising the step of determining a presence of an ischemic condition over a finite area of said medium.

34. The method of claim 29 further comprising the steps of applying said system to said physiological medium including transplanted cells of at least one of organs and tissues; and
   measuring said absolute value of at least one of said concentrations and said ratios thereof based on said $I_{mn}$, $I_{o,m}$, and $\epsilon_i$.

35. The method of claim 34 further comprising the step of determining a presence of an ischemic condition over a finite area of said medium.

36. The method of claim 29, wherein said eliminating step comprises the step of:
approximating unknown equation parameters as constants.

37. The method of claim 29, wherein said obtaining step comprises the step of irradiating said first and second set of electromagnetic waves having at least one of different wavelengths, phase angles, amplitudes and harmonics.

38. The method according to claim 37, wherein said irradiating step comprises the steps of:
providing said first set of electromagnetic waves with a first wavelength; and
providing said second set of electromagnetic waves with a second wavelength which is different from said first wavelength.

39. The method of claim 29, wherein said eliminating step comprises the step of:
taking at least one first ratio of two wave equations both selected from one of said first and second sets of wave equations.

40. The method of claim 39, wherein said eliminating step comprises the step of:
solving said wave equations for the same wave source with different wave detectors, thereby eliminating $\alpha_n$, $\gamma$, and $\sigma$ from said first ratio.

41. The method of claim 39, wherein said eliminating step comprises the step of:
solving said wave equations for at least two different wave sources and one wave detector, thereby eliminating $\beta_n$, $\gamma$, and $\sigma$ from said first ratio.

42. The method of claim 39, wherein said eliminating step comprises the step of:
taking at least one second ratio of two wave equations both selected from the other of said first and second sets of wave equations.

43. The method of claim 42, wherein said eliminating step comprises the step of:
obtaining at least one of a sum of and a difference between said first and second ratios so as to eliminate at least one of $\alpha_m$ and $\beta_n$ therefrom.

44. The method of claim 29, wherein said providing step comprises the step of:
expressing a formula of said medium-dependent and said geometry-dependent parameters as a polynomial of at least one of said concentrations.

45. The method of claim 44, wherein said polynomial includes a zero-th order term.

46. The method of claim 29, wherein said providing step comprises the step of approximating at least one medium-dependent or geometry-dependent parameter as a constant.

47. A method for determining concentrations of chromophores in a physiological medium using a system having at least one wave source and at least one wave detector using a mathematical expression having the form:

$$I_{mn} = \alpha_m \beta_n \gamma I_{o,m} \exp\{-B_{mn} L_{mn} \delta \Sigma_i (\epsilon_i C_i) + \sigma\},$$

wherein $I_{o,m}$ is a variable representing an intensity of electromagnetic waves irradiated by an m-th wave source, $I_{mn}$ is a variable for an intensity of electromagnetic waves irradiated by said m-th wave source and detected by an n-th wave detector, $\alpha_m$ is a parameter associated with at least one of said m-th wave source and medium, $\beta_n$ is a parameter associated with at least one of said n-th wave detector and medium, $\gamma$ is one of a proportionality constant and a parameter associated with at least one of said m-th wave source, n-th wave detector, and medium, $B_{mn}$ is a parameter accounting for lengths of optical paths of electromagnetic waves through said medium and associated with at least one of said m-th wave source, n-th wave detector, and medium, $L_{mn}$ is a parameter accounting for a distance between said m-th wave source and n-th wave detector, $\delta$ is a one of a proportionality constant and a parameter associated with at least one of said m-th wave source, n-th wave detector, and medium, $\epsilon_i$ is a parameter accounting for an optical interaction between electromagnetic waves and an i-th chromophore in said medium, $C_i$ is a variable for concentration of said i-th chromophore, and $\sigma$ is one of a proportionality constant and a parameter associated with at least one of said m-th source, n-th detector, and medium, said method comprising the steps of:

irradiating a first and second set of electromagnetic waves having different wave characteristics and measuring signals received from the medium to obtain at least two sets of equations relating the measured signals with unknown parameters in the wave equation;

eliminating at least one of $\alpha_m$, $\beta_n$, $\gamma$, $\delta$, and $\sigma$ from the obtained wave equations;

defining parameters of the mathematical expression including $B_{mn}$ and $L_{mn}$ as a function of at least one of said concentrations; and determining concentrations of chromophores in a physiological medium.

48. The method of claim 47 further comprising the step of obtaining values of said intensities of electromagnetic waves and said extinction coefficients of said chromophores.

49. The method of claim 48 further comprising the step of obtaining the absolute value of at least one of said concentrations and said ratios thereof.

* * * * *